United States Patent [19]

Kawasaki et al.

[11] Patent Number: 5,556,970
[45] Date of Patent: Sep. 17, 1996

[54] LANOLIN FATTY ACIDS, A METHOD FOR THEIR FRACTIONATION, COSMETICS AND DRUGS FOR EXTERNAL USE

[75] Inventors: Toshiyuki Kawasaki; Isao Kato; Kenji Noda; Masakatsu Osaki; Katsuhiko Miyazaki, all of Kakogawa; Hidekazu Nayeshiro, Daito; Hideya Ando, Kobe, all of Japan

[73] Assignee: Yoshikawa Oil & Fat Co., Ltd., Osaka, Japan

[21] Appl. No.: 167,825

[22] PCT Filed: Apr. 26, 1993

[86] PCT No.: PCT/JP93/00540

§ 371 Date: Dec. 22, 1993

§ 102(e) Date: Dec. 22, 1993

[87] PCT Pub. No.: WO93/22410

PCT Pub. Date: Nov. 11, 1993

[30] Foreign Application Priority Data

Apr. 27, 1992 [JP] Japan ................................. 4-107486
Jul. 23, 1992 [JP] Japan ................................. 4-239935
Nov. 26, 1992 [JP] Japan ................................. 4-316845

[51] Int. Cl.$^6$ ......................................... C11B 11/00
[52] U.S. Cl. ........................ 554/190; 552/545; 554/213
[58] Field of Search ........................... 554/190, 213; 552/545

[56] References Cited

U.S. PATENT DOCUMENTS 2,610,197 7/1947 Cunningham .......................... 554/190

2,862,943 12/1958 Wheeler ................................. 260/119
4,138,416 2/1979 Karesowa et al ................... 260/397.25

FOREIGN PATENT DOCUMENTS

0555776A1 8/1993 European Pat. Off. .
54-21207 7/1979 Japan .
55-160742 12/1980 Japan .

Primary Examiner—Gary Geist
Assistant Examiner—Deborah D. Carr
Attorney, Agent, or Firm—Armstrong, Westerman, Hattori, McLeland & Naughton

[57] ABSTRACT

The invention provides a process comprising treating a lanolin fatty acid with boric acid to convert hydroxy fatty acids therein to boric acid esters, subjecting the reaction mixture to vacuum distillation to fractionate the boric acid esters of hydroxy fatty acids from non-hydroxy fatty acids, hydrolyzing the boric acid esters, and subjecting the hydrolysate to vacuum distillation to provide α-hydroxy fatty acids and ω-hydroxy fatty acids, the resultant respective lanolin fatty acids and esters, and cosmetic products and drug products for external use containing them.

According to the invention, pale-colored, substantially odor-free lanolin fatty acids can be obtained easily and with high efficiency and these compounds can be effectively utilized in the pharmaceutical and cosmetic field.

19 Claims, No Drawings

LANOLIN FATTY ACIDS, A METHOD FOR THEIR FRACTIONATION, COSMETICS AND DRUGS FOR EXTERNAL USE

TECHNICAL FIELD

The present invention relates to a process for fractionating a lanolin fatty acid, more particularly a process for fractionating a lanolin fatty acid (hereinafter referred to briefly as LF) or its ester with a $C_{1-4}$ lower alcohol into a hydroxy fatty acid fraction (hydroxy fatty acids or their esters with the $C_{1-4}$ lower alcohol; hereinafter referred to briefly as HY) and a non-hydroxy fatty acid fraction (hydroxy-free fatty acids or their esters with the $C_{1-4}$ lower alcohol; hereinafter referred to briefly as NH) and further fractionating said HY into an α-hydroxy fatty acid fraction (hereinafter ALF) and an ω-hydroxy fatty acid fraction (hereinafter WHY), the resultant lanolin fatty acids and their esters, and cosmetics and drugs for external use which contain them.

PRIOR ART

LF available from the saponification of wool grease secreted on the surface of wool, for instance, comprises iso- and anteiso-non-fatty acids accounting for about ⅔ and hydroxy fatty acids accounting for about ⅓. This LF is extremely lean in normal fatty acids which are predominant among naturally-occurring fatty acids and contains even-number acids and odd-number acids in appropriately equal proportions. The typical composition is shown in Table 1. In the following description, % represents % by weight unless otherwise indicated.

TABLE 1

| Composition | | Content (%) |
|---|---|---|
| Non-hydroxy acids | Normal | 12.1 |
| | Iso | 22.1 |
| | Anteiso | 26.3 |
| α-Hydroxy acids | Normal | 21.8 |
| | Iso | 4.5 |
| | Anteiso | 0.8 |
| ω-Hydroxy acids | Normal | 3.0 |
| | Iso | 0.8 |
| | Anteiso | 1.3 |
| Unsaturated acids | | 2.1 |
| Polyhydroxy acids | | 4.7 |
| Total | | 99.5 |

The dominant proportion of $C_{10-36}$ hydroxy fatty acids accounting for about 30–35% of LF is comprised of $C_{16}$ α-hydroxy fatty acid. Short-chain hydroxy fatty acids such as lactic acid, citric acid, tartaric acid, etc. have been found to be laudable in emulsifying and humectant actions and be effective in atopic dermatitis, ichthyosis and reduction of age-associated wrinkles but there has been no information on the actions of long-chain hydroxy fatty acids such as those mentioned above. Moreover, ω-hydroxy fatty acids constituting another fraction of LF are constituents of o-acylceramides which are reportedly playing a key role in the humectant function of the horny layer of the skin but the activities of such ω-hydroxy fatty acids and their esters with lower alcohols as such are not known.

α-Hydroxy fatty acids, ω-hydroxy fatty acids and their esters and other derivatives can find application not only in drugs, cosmetics and pharmaceutical preparations for external use but also in various other uses such as surfactants, waxes, lubricating greases and so on and the usage thereof is expected to expand further in the future. However, the only long-chain hydroxy fatty acid in common use today is 12-hydroxystearic acid and no other long-chain α- or ω-fatty acids are commercially available in independent and concentrated forms.

Heretofore, because of its characteristic animal odor and dark color which lanolin alcohols are not possessed of, LF has been rather shunned than welcomed by the cosmetic industry. Therefore, development of a technology for fractionating its constituent hydroxy fatty acid fraction and non-hydroxy fatty acid fraction from each other, which would overcome the above problems, and development of uses for the fractions has been earnestly awaited.

As a means for eliminating the animal odor and dark color of LF, a vacuum distillation process has so far been in use but this process is not capable of separating hydroxy fatty acids from non-hydroxy fatty acids.

Thus, in the regular distillation of LF, non-hydroxy fatty acids cannot be separated from hydroxy fatty acids and the distillate fatty acid fraction obtained in a yield of 26% after removal of the initial 3% cut, for instance, shows a composition of 57.3% non-hydroxy branched fatty acids and 18.8% hydroxy fatty acids and its melting point is 48.4° C. Similarly, the distillate fatty acid recovered in a yield of 68% contains 57.5% non-hydroxy fatty acids and 20.7% hydroxy fatty acids and its melting point is 52.9° C. Thus, by the ordinary distillation, it is impossible to achieve a hydroxy fatty acid content beyond 60%. In case LF is fractionated with a solvent into a low-melting fraction and a high-melting fraction, too, the hydroxy fatty acid content of the low-melting fraction (m.p.≦40° C.) is 13–30%. Thus, hydroxy fatty acids cannot be separated from non-hydroxy fatty acids by the solvent fractionation technique, either.

Aside from the foregoing, there has been proposed a method which comprises converting LF to methyl ester, dissolving it in benzene-petroleum ether and achieving fractionation using an alumina column, a method comprising fractional elution of the ethyl or methyl ester of LF from a chromatographic column using petroleum benzin as the solvent, a method of fractional purification by the alumina suspension technique or a method comprising separating hydroxy fatty acids by multi-stage liquid-liquid extraction. However, all of these methods are low in productivity and not practically useful.

As regards end-uses for LF, JP Kokai H4-164014 discloses that a low-melting LF having a melting point not exceeding 40° C. and containing not less than a total of 30% of iso- and anteiso-fatty acids of not more than 19 carbon atoms is effective as a hairdressing material. However, the technology disclosed in the literature employs a mixture of non-hydroxy fatty acids and hydroxy fatty acids as it is, viz. without fractionation, and, moreover, it is logical that the melting point of any LF containing not less than a total of 30% of iso- and anteiso-fatty acids of not more than 19 carbon atoms cannot be higher than 40° C. Therefore, the disclosure is not more than equivalent to arguing that a low-melting LF having a melting point not exceeding 40° C. can be an effective cosmetic material. Moreover, in view of the starting material composition, the disclosed production process and examples (Table 2 in the specification) and the presence of ω-fatty acids of not less than 26 carbon atoms, it seems reasonable to assume that the proportion of hydroxy fatty acids in said low-melting LF is in the range of 13–30%.

DISCLOSURE OF THE INVENTION

It is an object of the present invention to provide a novel industrial technology for eliminating the animal odor and dark color of LF to meet the industry's demand and enabling separation of hydroxy fatty acids in LF from the concomitant non-hydroxy fatty acids.

Another object of the invention is to provide a novel hydroxy fatty acid composition and a non-hydroxy fatty acid composition, which are different in composition from the low-melting LF disclosed in the above-mentioned literature.

It is a further object of the invention to provide various ester derivatives of said hydroxy fatty acids and non-hydroxy fatty acids.

A still another object of the invention is to provide the use of said hydroxy fatty acids, non-hydroxy fatty acids and their ester derivatives as active ingredients of cosmetic products and drugs for external use.

After an intensive research endeavour to accomplish the objects, the inventors of the invention found that the hydroxy fatty acid fraction (HY) occurring in LF and/or its ester with a lower alcohol can be separated from the non-hydroxy fatty acid fraction (NH) by subjecting the former serially to conversion to boric acid ester and vacuum distillation and that said boric acid ester of HY can be hydrolyzed to HY which, in turn, can be fractionated by vacuum distillation into a pure α-hydroxy fatty acid fraction (ALF) and a pure ω-hydroxy fatty acid fraction (WHY).

The inventors further found that each of said HY, NH, ALF and WHY fractions has its own satisfactory characteristics for use as a material for cosmetic products and pharmaceutical products for external use and that their esters, for example sterol esters, also have their own characteristic physical properties suited for cosmetic and topical drug products.

The present invention has been developed on the basis of the above findings.

Thus, the invention provides a process which comprises treating a lanolin fatty acid selected from LF and its $C_{1-4}$ lower alcohol ester derivatives with boric acid to convert HY in said lanolin fatty acid to the boric acid ester and then subjecting the reaction mixture to vacuum distillation to separate said boric acid ester of HY from the NH contained in said lanolin fatty acid and a process comprising hydrolyzing said boric acid ester of HY to HY and subjecting the reaction mixture to vacuum distillation to fractionate ALF and WHY.

The invention further provides cosmetic products and drugs for external use each containing any of said NH, HY, ALF and WHY, salts thereof, and ester derivatives thereof.

The processes of the invention are now described in detail. LF, the starting material for use in the process of the invention for the fractionation of NH and HY, may be a fraction separated from lanolin by any known method, a purified fraction obtainable from said fraction by the ordinary procedure or the remainder of such a fraction after separation and recovery of its partial fraction such as an ω-hydroxy fatty acid fraction or a non-hydroxy fatty acid fraction. The $C_{1-4}$ lower alcohol ester of such LF includes esters with methanol, ethanol, propanol, isopropanol, butanol, isobutanol, etc. and these esters can be obtained by esterifying said LF in the conventional manner. Furthermore, the starting material for the invention may be a mixture of said LF and esters thereof.

In this process of the invention, said lanolin fatty acid is treated with boric acid to convert the hydroxyl groups of HY, namely hydroxy fatty acids and lower alcohol esters thereof, which are contained therein to boric acid esters. Boric acid which is used for this boric acid treatment may for example be boric acid ($H_3BO_3$) or boric anhydride ($B_2O_3$) but boric acid is preferred from cost consideration. This boric acid treatment is carried out using about 0.5–5 equivalents (based on the reaction equivalent determined from the hydroxyl value of the starting material fatty acid; the same applies hereinafter), preferably about 1–3 equivalents, of boric acid per equivalent of the starting material fatty acid fraction at a temperature of about 50°–150° C., preferably about 100°–120° C., for about 0.5–8 hours. When the proportion of boric acid is less than the above range, unreacted HY is included in NH to lower the purity of NH. Conversely, when boric acid is used in excess of the above equivalent range, it entails a time-consuming procedure for removal of the excess unreacted boric acid. When the reaction temperature is lower than the above range, either the esterification reaction does not proceed to a sufficient extent or the reaction time is prolonged. On the other hand, the reaction at a high temperature beyond the range tends to cause the undesirable coloration. While this esterification reaction with boric acid can be conducted optionally at atmospheric pressure or under reduced pressure but is preferably carried out under a reduced pressure of not more than 100 Torr, preferably in the range of about 30-1 Torr, with the byproduct water being removed. The lower the pressure is, the shorter is the reaction time required.

By the above boric acid treatment, HY in the starting material lanolin fatty acid is converted to the boric acid ester. By subjecting this boric acid ester to distillation under reduced pressure, the ester can be easily separated from NH, namely non-hydroxy fatty acids and their lower alcohol esters.

Therefore, in this process of the invention, as the above reaction mixture is further subjected to vacuum distillation, the boric acid ester of HY is separated from NH. This vacuum distillation can be carried out by the conventional procedure. The degree of vacuum is generally not more than 1 Torr and preferably chosen from the range of about 0.5–0.001 Torr. The lower the pressure is, the greater is the reduction of distillation temperature so that the coloration and evolution of odor of the distillate can be prevented. The distillation temperature is generally not higher than about 250° C. and preferably selected from the range of about 120°–200° C. The temperature influences the yield of distillation and when the temperature is within the above-mentioned range, the distillation yield is about 70% or less, generally in the range of 30–60%, and the desirable fractionation effect of the invention is well implemented. However, when the temperature is increased too high, viz. beyond 250° C., the distillation yield is increased too much that a contamination of HY into NH becomes remarkable to detract from the product purity. By choosing the proper distillation temperature within the above range, HY and NH satisfactory in color, melting point, purity, etc. can be easily fractionated and recovered.

The NH thus obtained may at times contain the unreacted boric acid and the boric acid ester of HY but they can be removed by a procedure similar to the procedure for removal of residual boric acid from HY which will be described hereinafter and the resultant pure product can be utilized in various uses. Moreover, the boric acid ester of HY can be subjected to hydrolysis reaction, for instance, to eliminate the boric acid in the per se conventional manner to provide a product which is also suited for various uses.

The hydrolysis reaction mentioned above can be carried out in the same manner as ordinary hydrolysis reactions. To be specific, the reaction can be carried out using a solvent comprising water and an organic solvent such as, for example, an alcohol, e.g. methanol, ethanol, propanol, isopropyl alcohol, butyl alcohol, etc., or a ketone, e.g. acetone, methyl ethyl ketone, methyl isopropyl ketone, etc. This hydrolysis reaction can also be carried out by dissolving the substrate boric acid ester of HY in a suitable water-immiscible solvent such as hexane, heptane, benzene, toluene or the like and extracting the desired fraction from the resultant solution by means of said solvent.

The resultant HY contains ALF and WHY, both of which have important uses, and according to the research of the inventors, these fractions can be separated from each other and recovered by subjecting the above hydrolyzate to vacuum distillation. Therefore, the invention further provides a process for fractional recovery of ALF and WHY.

This fractionation of ALF and WHY according to the invention can be carried out by a vacuum distillation procedure similar to that described for the fractionation of NH and HY and the usable degree of vacuum, distillation temperature and appropriate distillation yield are similar to those mentioned above. Thus, the degree of vacuum is not more than about 1Torr and preferably in the range of about 0.5–0.001Torr and the distillation temperature is not higher than about 250° C. and preferably in the range of about 120°–200° C. and the distillation yield under these conditions is not greater than about 60% and preferably about 20–50%. In this vacuum distillation, the lower the distillation temperture is and the lower the distillation yield is, the higher is the ALF content of the distillate, while the higher the distillation temperature and the higher the distillation yield, the higher is the recovery rate of WHY.

The fatty acid composition and physical properties of each of the fractions thus obtained in accordance with the invention can be summarized as follows.

<NH>

It contains 30–45% of iso-fatty acids of the following formula I, 30–50% of anteiso-fatty acids of formula II and 10–30% of normal fatty acids of formula III, the sum of said iso-fatty acids and anteiso-fatty acids accounting for at least 60%, with a hydroxy fatty acid content of less than 10%.

Formula I: Iso-fatty acids $$CH_3-CH(CH_2)_n-COOH$$
$$|$$
$$CH_3 \qquad n=6-26$$

Formula II: Anteiso-fatty acids $$CH_3-CH_2-CH(CH_2)_n-COOH$$
$$|$$
$$CH_3 \qquad n=6-26$$

Formula III: Normal fatty acids $$CH_3-(CH_2)_n-COOH \qquad n=8-28$$

Particularly, of the above-mentioned NH, free forms of NH have melting points (Japanese Standards of Cosmetic Ingredients, Method 2) in the range of about 25°–55° C., acid values (AV) in the range of about 140–210 and saponification values in the range of about 160–210.

<HY>

It contains at least 60% of α-hydroxy fatty acids of not less than 14 carbon atoms, of which normal α-hydroxy fatty acids of the following formula IV account for 50–70%, iso-α-hydroxy fatty acids of formula V accounts for 10–30% and anteiso-α-hydroxy fatty acids of formula VI accounts for 0–15%, with an ω-hydroxy fatty acid content of 0–15%. The saponification values are in the range of about 160–210 and the melting points of free forms of HY (Japanese Standards of Cosmetic Ingredients, Method 4) exceed 40° C. and are substantially within the range of 50°–85° C.

Formula IV: Normal fatty acids $$CH_3-(CH_2)_n-CH-COOH$$
$$|$$
$$OH \qquad n=11-22$$

Formula V: Iso-fatty acids $$CH_3-CH(CH_2)_{2n-1}-CH-COOH$$
$$| \qquad\qquad |$$
$$CH_3 \qquad\quad OH \qquad n=5-10$$

Formula VI: Anteiso-fatty acids $$CH_3-CH_2-CH-(CH_2)_{2n-1}-CH-COOH$$
$$| \qquad\qquad\qquad\qquad |$$
$$CH_3 \qquad\qquad\qquad OH \qquad n=4-10$$

(ALF)

It contains at least 60% of α-hydroxy fatty acids of not less than 14 carbon atoms, of which normal fatty acids of the above formula IV account for 50–70%; iso-fatty acids of formula V account for 10–30% and anteiso-fatty acid of formula VI account for 0–15%, with an ω-hydroxy fatty acid content of 0–5%. The saponification values are substantially within range of 165–210 and the melting points (free forms, the above standard, Method 4) are higher than 40° C. and are substantially within the range of 55°–85° C.

Thus, by the method of the invention, HY and NH can be fractionated and purified from LF in high purity in an expedient manner and ALF and WHY differing in the position of hydroxyl group can then be separated and purified from said HY by concentration in high purity. The resultant respective fatty acid fractions are not only available from a natural source but are pale in color and substantially odorless. Furthermore, NH is composed by hydroxyl-free predominantly branched-chain substances, while HY is composed of polar hydroxyl groups. ALF, purified as above, is composed of hydroxy fatty acids having a hydroxyl group in the α-position, while WHY are hydroxy fatty acids having a hydroxyl group in the terminal ω-position.

By the method of the invention, the unsaponifiable materials occurring in the conventional LF are esterified concurrently in the conversion to acid esters and become less volatizable in the subsequent vacuum distillation so that they are easily separated from the NH fraction. On the other hand, the unsaponifiable materials concentrated in the HY fraction can be finely removed by the subsequent vacuum distillation so that the concentration of unsaponifiables in the final HY fraction is not high.

Each of the respective fatty acids (free acids) can be converted to a salt by the conventional method utilizing its carboxyl group. The salt includes water-soluble salts, namely alkali metal salts such as salts with sodium, potassium, etc., alkali metal salts such as salts with magnesium, calcium, etc., ammonium salts, amine salts such as mono-, di- and triethanolamine salts, salts with morpholine and so on.

The resultant NH, HY, ALF and WHY and salts thereof respectively have the aforementioned characteristics and can be incorporated, independently or in combination, in drugs and quasi drugs for external use, or cosmetics such as skin cosmetics, hair cosmetics, makeup cosmetics, etc. in which the following effects can be expected. The hair cosmetics mentioned above are cosmetic preparations for application to the hair and include hair tonics, hair lotions, hair creams, shampoos and rinses. The makeup cosmetics are cosmetic preparations for application to the face, inter alia, for purposes of makeup and include foundations, rouges, mascaras, eyeshadows and so on. The skin cosmetics are various cosmetic preparations for application to parts of the body other than the parts mentioned above and include creams, lotions, bath toiletry products and so on.

Thus, NH and its salt, which are rich in branched fatty acids, are well spreadable and able to form a thin film on the surface of the skin or scalp hair. Moreover, they do not interfere with percutaneous absorption but help to provide the skin and hair with gross and smoothness. In addition, because they do not contain hydroxyl groups, the formation of lactones and lactides which is inevitable with the conventional LF is not observed, thus contributing to the shelf life of external drugs and cosmetic products such as creams. Furthermore, since NH is composed of saturated fatty acids, it is little colored on heating and is excellent in oxidation resistance and thermal stability.

Therefore, the present invention further provides drugs for external use and cosmetics which contain NH or a salt thereof as an active ingredient. The external drugs and cosmetics according to the invention have excellent functional properties such as water repellency, thermal stability, stability against oxidation, the action to render the surface film of the skin porous and permeable to water vapor, the action to insure a smooth percutaneous respiration, the action to protect the hair, antimicrobial action, improved spreadability which insures the formation of a stable film on the surface of the skin or hair, the action to provide the film with good sheen and flexibility. Thus, when used in external drugs, skin cosmetics and hair cosmetics, they impart such qualities as smoothness of the skin and combing response of the hair. In addition to the above qualities, NH is further excellent in the dispersibility of dyes and pigments so that the cosmetics of the invention, for example makeup cosmetics, import good feeling of use such as spreadability and good sheen. Moreover, unlike the conventional LF, NH does not produce the lactones and lactides associated with hydroxyl groups so that the cosmetic products of the invention containing this fraction are characterized by good aging resistance.

HY and its salt which are predominantly composed of α-hydroxy fatty acids are excellent in emulsifiability and moisture retention and, therefore, are effective for the moisture retention of the horny layer of the skin and of the hair cuticles, thus being expected to be useful for the prevention of desiccation of the skin and hair. Moreover, since the HY contains hydroxyl groups, it is highly soluble in polar substances.

Therefore, the invention further provides drugs for external use and cosmetics containing said HY and its salts, ALF and WHY which are fractionated therefrom and their salts. Because all of said HY, ALF and WHY have excellent emulsifying and humectant properties and are effective in retaining the moisture of the skin and hair, thus being useful for the prevention of drying of the skin and hair and the stabilization of creams, besides being compatible with polar solvents, the external drugs and cosmetics containing them in accordance with the invention are effective topical drugs, skin-care and hair-care cosmetics.

Particularly a mixture of NH or a salt thereof and HY or a salt thereof, that is to say a composition containing 40% or more of NH, can be freely adjusted as to the degree of manifestation of the respective fractions mentioned above and, therefore, when incorporated in a skin cosmetic or a hair cosmetic, provides a still more effective cosmetic preparation.

Furthermore, ALF according to the invention, namely a fatty acid fraction, inclusive of its salt, which contains at least 60% of α-hydroxy fatty acids displays outstanding efficacy for the protection and growth promotion of the scalp and hair so that cosmetic products effective for prevention of hair graying, for growth promotion of hair, for activation of epidermal cells and for antidandruff purposes can be obtained by incorporating said ALF.

The inventors of the present invention further found that said HY and ALF and their salts have the activity to significantly accelerate the proliferation of epidermal cells. Particularly, their subsequent research into ALF and its salt revealed that this fraction not only ameliorates the function of the horny layer but has the activity to promote melanin production to help prevent graying of hair and further contributes to promotion of hair growth and prevention of dandruff. In this respect, too, the ALF and salt according to the invention are suitable for cosmetic products designed for prevention of graying, protection and growth promotion of the scalp and scalp hair, namely anti-graying, hair grower, epidermal cell activating or antidandruff cosmetics.

Except that the HY, NH, ALF and WHY, inclusive of their salts, are used, the external drugs and cosmetic products of the invention can be manufactured by the per se known procedures. There is no particular limitation on the proportion of said active fractions. Generally speaking, the proportion in external drugs is about 0.1–50% (by weight, the same applies hereinafter), preferably not more than about 10%, that in creamlike cosmetic products is about 0.1–50%, preferably not more than about 15%, that in nonaqueous makeup cosmetic systems is about 0.1–80%, preferably about 1–40%, that in aqueous makeup cosmetic systems is about 0.1–50%, that in nonaqueous oil-type hair cosmetic products is about 0.1–90%, and that in nonaqueous creamlike hair cosmetic products is about 0.1–50% and that in shampoos, rinses and other products is about 0.1–10%.

The present invention further provides a fatty acid composition equivalent to that obtainable by the above-described method of the invention and having the following characteristics.

Thus, the invention provides a non-hydroxy fatty acid (hereinafter referred to briefly as free NH) composition derived from a lanolin fatty acid containing 30–45% of iso-fatty acids of formula I, 30–50% of anteiso fatty acids of formula II and 10–30% of normal fatty acids of formula III, the sum of said iso- and anteiso-fatty acids being at least 60%, with a hydroxy fatty acid content of less than 10% and a hydroxy fatty acid (hereinafter referred to as free HY) composition derived from lanolin and containing at least 60% of α-hydroxy fatty acids of not less than 14 carbon atoms, of which normal α-hydroxy fatty acids of formula IV account for 50–70%, iso-α-hydroxy fatty acids of formula V for 10–30% and anteiso-fatty acids of formula V for 0–15%, with an ω-hydroxy fatty acid content of 0–15%.

The above-mentioned free NH composition of the invention is characterized in that the melting points (Japanese Standards of Cosmetic Ingredients, Method 2) are about 25°–55° C., acid values (AV) in the range of 140–210 and SV in the range of about 160–210. On the other hand, the above-mentioned free HY composition is characterized in that the SVs are in the range of about 160–210 and melting points (Japanese Standards of Cosmetic Ingredients, Method 4) are higher than 40° C. and substantially in the range of 50°–85° C.

The free HY and free NH according to the invention can be respectively converted to ester derivatives by reacting them with a suitable alcohol utilizing their carboxyl groups. The ester derivatives include sterol esters, sugar esters, 2-ethylhexanol esters, higher alcohol esters and polyhydric alcohol esters. These ester derivatives can also be obtained by transesterification reaction with lower alcohol esters of the respective fatty acids.

The ester derivatives are now described in further detail below. The sterol esters can be produced by using various sterols of animal, vegetable or synthetic origin. Among typical sterols are cholesterol, lanosterol, dihydrolanosterol and, as mixtures thereof, isocholesterol, sitosterol, stigmasterol, campesterol, phytosterol, desmosterol, 7-dehydrocholesterol and reduction products thereof, and these sterols can be used alone or in combination.

The conditions of the esterification reaction between the lanolin fatty acid (free HY and free NH) of the invention and any of the above sterols can be liberally selected from the range of esterification conditions heretofore employed. For example, a mixture of the starting fatty acid and sterol may be heated at a temperature of about 100°–250° C., either in the absence of or in the presence of a catalyst such as p-toluenesulfonic acid or tin chloride. The end-point of this reaction can be confirmed by acid value determination.

Where said HY or NH is a lower alkyl ester, the objective sterol ester can also be obtained by subjecting the fatty acid lower alkyl ester and sterol to transesterification reaction in the presence of a transesterification catalyst such as sodium methoxide.

The sugar ester includes esters with various monosaccharides such as glucose, fructose, mannitol, sorbitol, sorbitan and starch oligosaccharides such as starch sugars and sucrose. These sugar esters can also be produced by any of the various known production processes. By way of example, the desired sorbitol ester can be obtained by heating a mixture of the starting fatty acid and sorbitol, which is a saccharide, in the presence of sodium hydroxide, a catalyst, in a nitrogen gas stream at a reaction temperature of about 190° C. Similarly, the desired sorbitan ester can be obtained at a reaction temperature of about 230°–250° C. The sucrose ester can be obtained by the process using a solvent such as dimethylformamide (DMF) or dimethyl sulfoxide (DMSO) or the so-called microemulsion process in which the starting fatty acid material and sugar are reacted in an emulsion form in the presence of small amounts of an emulsifier.

The esterification reaction for the 2-ethylhexanol ester can also be carried out under the same conditions as those commonly employed. For example, a mixture of the starting fatty acid material and 2-ethyl-hexanol is heated, either in the absence of or in the presence of a catalyst such as p-toluenesulfonic acid, at a temperature of about 100°–180° C. The desired ester can also be produced by subjecting a fatty acid lower alcohol ester to ester interchange reaction in the presence of a transesterification catalyst such as sodium methoxide.

The higher alcohol ester includes esters of aliphatic alcohols of not less than 12 carbon atoms and can be produced in the same manner as the various kinds of esters mentioned above. The alcohol which is used for the production of this type of ester may be saturated or unsaturated and straight-chain or branched. The branched aliphatic (linear) alcohol includes, among others, iso-alcohols and anteiso-alcohols of the following formula VII and VIII; a mixture of such alcohols, for example Lanolin Alcohol HH (a sterol-free aliphatic higher alcohol-glycol mixture available by solvent fractionation of lanolin alcohols; Yoshikawa Oil and Fat Co., Ltd), synthetic branched alcohols such as hexadecyl alcohol available from Esso Standard, NJCOL 160A, 160B, 181A, 200A and 200C (all manufactured by New Japan Chemical Co. Ltd.), Fine Oxocol 1800 (Nissan Chemical Industries, Ltd.), octyldodecanol available from Henkel International GmbH, and so on.

Formula VII: Iso-alcohol

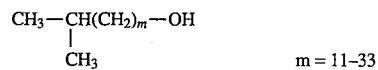

$m = 11–33$

Formula VIII: Anteiso-alcohol

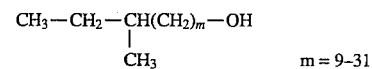

$m = 9–31$

The polyhydric alcohol ester is any ester of an alcohol (exclusive of sugar) of not more than 10 carbon atoms and having 2 or more hydroxyl groups per molecule. This ester includes, as typical species, the glycerol ester, pentaerythritol ester, dipentaerythritol ester and trimethylolpropane ester.

These polyhydric alcohol esters can also be produced in the same manner as the respective kinds of ester derivatives mentioned above. For example, the glycerol ester can be produced by the process described in J.A.O.C.S., Vol. 62, 1575, 1985. The pentaerythritol ester and dipentaerythritol ester can be produced under heating at about 200°–250° C., preferably about 230°–240° C., in a nitrogen stream with stirring.

The above free NH composition and free HY composition and the corresponding ester derivatives according to the invention respectively have distinct characteristics derived from the starting fatty acid material and, in addition, each of the ester derivatives has characteristics derived from the corresponding starting alcohol material. All of these compositions and ester derivative compositions are of value in drugs for external use and cosmetic products. The usefulness of said free NH fraction and free HY fraction has already been pointed out hereinbefore.

The usefulness of the ester derivatives as ingredients of external drugs or cosmetics is now described. By way of illustration, the cholesterol ester of free HY fraction of the invention is excellent in emulsifiability, hydration potential and moisture retention property and the cholesterol ester of the free NH fraction is highly compatible with the skin, easily absorbable into the skin and does not cause a sticky sensation to the skin.

The glycerol esters of free NH fraction and free HY fraction according to the invention can be incorporated in a base for an external drug, a skin-care cosmetic preparation or a hair-care cosmetic preparation to impart smoothness to the skin, good hair manageability and other excellent feels. Furthermore, these help to overcome the problem of allergy which is associated with lanolin and lanolin alcohols.

Particularly the free NH fraction, unlike the ordinary LF, does not undergo lactonization or lactide formation due to hydroxyl groups and, therefore, impart longer shelf lives to products when incorporated. By fractionating LF into such free NH and free HY fractions, it is possible to provide novel bases for external drugs and skin-care or hair-care cosmetic preparations exploiting the respective characteristics of the component fatty acids to impart moist and refreshing feels to the skin and hair far more effectively than the conventional glycerol ester of unfractionated LF.

The 2-ethylhexanol ester of free NH fraction of the invention has an improved compatibility with nonpolar oils without being compromised in the inherent characteristics of free NH, is low in specific gravity and viscosity and ready to be absorbed, and when used as an oleaginous base for cosmetic preparations, insures a supple feel without leaving an greasy handle. On the other hand, the 2-ethylhexanol ester of free HY of the invention retains the characteristics of the free NY and yet has an improved compatibility with polar solvents and a good affinity for the skin to impart characteristic softness and moist handle to the skin.

The pentaerythriol and dipentaerythritol esters of the free NH and free HY fractions of the invention are free from the problem of allergy which is sometimes encountered with lanolin alcohols and on the strength of the respective characteristics of free NH and free HY, offer excellent spreadability on the skin and a good affinity for the skin with the consequent refreshing and conditioning effects on the skin or a good comb-through effect to the hair, besides insuring an improved shelf life to cosmetic and other preparations.

The sugar esters of free NH and free HY fractions of the invention offer a freedom of control over the monoester content and, as safe surfactants with varying HLB numbers, can be advantageously incorporated in cosmetic preparations and drug products for external use.

Furthermore, the higher alcohol esters of free NH and free HY of the invention are low in cloud point and show excellent spreadability on the skin and a high compatibility with various polar solvents. Therefore, as esters which do not interfere with the respiratory function of the skin and offer high fluidity at low temperatures, they can be used advantageously in lieu of liquid paraffin which is commonly in use in the cosmetic industry.

As regards the modes of utilization of the above respective ester derivatives in external drugs and cosmetics, these derivatives can be used in substantially the same manner as the HY, NH, ALF and WHY fractions of the invention and in substantially the same proportions as mentioned for the latter fractions in various formulations.

BEST MODE OF CARRYING THE INVENTION INTO PRACTICE

The following examples are intended to describe the invention in further detail and should by no means be construed as defining the scope of the invention. The physical properties of the products obtained in the respective examples were determined in accordance with Japanese Standards of Cosmetic Ingredients and unless otherwise specified, melting point data were generated by Method 2 (ascending melting point) of the same Standards.

Examples 1–13, shown below, pertain to the fractionation of lanolin fatty acid.

Example 1

To 674.3 g of a lanolin fatty acid methyl ester (hydroxyl value 49.4) was added 45.2 g of boric acid ($H_3BO_3$) and the reaction was conducted under reduced pressure at 110° C. for 6 hours. This reaction mixture, 354.2 g, was further subjected to vacuum distillation (170° C., 0.1 Torr) to recover 141.2 g (recovery rate 39.9 wt. %) of non-hydroxy fatty acid methyl ester (S1) as the main fraction and 213.0 g (recovery rate 60.1 wt. %) of boric acid ester of hydroxy fatty acid methyl ester as the residue.

The above boric acid ester of hydroxy fatty acid methyl ester was hydrolyzed and rinsed to remove the boric acid and provide a hydroxy fatty acid methyl ester (S2).

The analyses of S1 (rinsed to remove contaminant boric acid) and S2, obtained above, are shown below.

It should be understood that the evaluation of odor was carried out by a sensory test panel of 10 assessors according to the following rating scale with the evaluation of the starting lanolin fatty acid being used as the reference (the mean rating by the assessors is shown).

⊙—Marked improvement, substantially odor-free o—Improvement, the characteristic odor of lanolin fatty acids still noted x—No improvement The purity was analyzed by gas chromatography.
<Non-hydroxy fatty acid methyl ester (S1)>
Color (GH)≦1, acid value=0.2, SV=195.8, OH value=4.4, cloud point=21° C., unsaponifiable material=0.4 wt. %, odor=⊙, purity=90.3 wt. %.
<Hydroxy fatty acid methyl ester (S2)>
Color (GH)≧18, acid value=1.3, SV=169.6, OH value=83.2, m.p.=47.6° C.

Example 2

To 4750 g of the same lanolin fatty acid ester as used in Example 1 was added 318.7 g of boric acid and the reaction was carried out under the same conditions as described in Example 1. The reaction mixture, 4840 g, was subjected to vacuum distillation (190° C., 0.01 Torr) to recover 2500 g (recovery rate 51.7 wt. %) of non-hydroxy fatty acid methyl ester as the main fraction and 2340 g (recovery rate 48.3 wt. %) of boric acid ester of hydroxy fatty acid methyl ester. They were respectively purified in the same manner as in Example 1 to provide non-hydroxy fatty acid methyl ester (S3) and hydroxy fatty acid methyl ester (S4).

The S3 and S4 obtained above were analyzed as in Example 1. The results are shown below.
<Non-hydroxy fatty acid methyl ester (S3)>
Color (GH)=3, acid value=0.1, SV=173.1, OH value=15.1, POV=3.1, m.p.=30.6° C., unsaponifiable material=0.8 wt. %, odor=⊙, purity=89.1 wt. %, hydroxy fatty acid content=3.3 wt. %.
<Hydroxy fatty acid methyl ester (S4)>
Color (GH)≧18, acid value=2.5, SV=140.1, OH value=104.0, m.p.=43.6° C., purity=63.0 wt. %

Example 3

To 500 g of lanolin fatty acid ethyl ester (OH value=47.2) was added 45.3 g of boric acid and the mixture was treated in the same manner as Example 1 to provide the following ethyl esters.
<Non-hydroxy fatty acid ethyl ester (S5)>
Color (GH)=3, acid value=0.2, OH value=10.1, cloud point=20° C., unsaponifiable material=0.5 wt. %, odor=⊙, purity=89.8 wt. %
<Hydroxy fatty acid ethyl ester (S6)>
Color (GH)≧18, acid value=2.0, OH value=84.2, m.p.=46.3° C.

Example 4

To 400 g of lanolin fatty acid isopropyl ester (OH value=45.0) was added boric anhydride ($B_2O_3$) and the reaction was conducted under reduced pressure at 100° C. for 3 hours. The reaction mixture was further subjected to vacuum distillation (140° C., 0.5 Torr) to recover 157.9 g (recovery rate 39.4 wt. %) of non-hydroxy fatty acid isopropyl ester as the main fraction and 242.1 g (recovery rate 60.6 wt. %) of boric acid ester of hydroxy fatty acid isopropyl ester as the residue. These products were purified as in Example 1 to provide the following non-hydroxy fatty acid isopropyl ester (S7) and hydroxy fatty acid isopropyl ester (S8).
<Non-hydroxy fatty acid isopropyl ester (S7)>

Color (GH)≦1, acid value=0.2, SV=139.3, OH value=9.7, cloud point=12° C., unsaponifiable material=0.8 wt. %, odor=☉, purity=89.9 wt. %.

<Hydroxy fatty acid isopropyl ester (S8)>
Color (GH)≧18, acid value=0.3, SV=139.3, OH value= 77.5, m.p.=57.2° C., purity=61.4 wt. %.

Example 5

To 500 g of lanolin fatty acid butyl ester (OH value=42.8) was added 45.0 g of boric acid and the mixture was treated under the same conditions as Example 1 to provide the following butyl esters.

<Non-hydroxy fatty acid butyl ester (S9)>
Color (GH)=3, acid value=0.3, OH value=8.1, cloud point= 12° C., unsaponifiable material=0.8 wt. %, odor=☉, purity= 89.1 wt. %.

<Hydroxy fatty acid butyl ester (S10)>
Color (GH)≧18, acid value=1.5, OH value=74.0, m.p.= 58.4° C.

Example 6

To 500 g of lanolin fatty acid (OH value=50.1) was added 18.4 g of boric acid and the reaction was carried out under reduced pressure at 120° C. for 6 hours. The reaction product, 383.5 g, was further subjected to vacuum distillation (170° C., 0.02 Torr) to recover 93.2 g (recovery rate 24.3 wt. %) of non-hydroxy fatty acid as the main fraction and 290.3 g (recovery rate 75.7 wt. %) of hydroxy fatty acid boric ester as the residue. These products were respectively purified as in Example 1 to provide the following non-hydroxy fatty acid (S11) and hydroxy fatty acid (S12).

<Non-hydroxy fatty acid (S11)>
Color (GH)=3, acid value=195.3, SV=199.7, OH value= 13.0, m.p.=34.7° C., unsaponifiable material=1.6 wt. %, odor=☉, purity = 89.4 wt. %.

<Hydroxy fatty acid (S12)>
Color (GH)≧18, acid value=68.7, SV=157.4, OH value= 53.1, m.p.=60.6° C.

Example 7

In 1000 ml of n-hexane was dissolved 500 g of the boric acid ester of hydroxy fatty acid methyl ester obtained in Example 2 at elevated temperature. The solution was then washed with 4 portions of 300 ml each of aqueous methanol to cleave the boric acid ester and thereby remove the boric acid, and the n-hexane was then removed to provide 390 g of hydroxy fatty acid methyl ester (OH value=104.0).

This hydroxy fatty acid methyl ester was subjected to vacuum distillation (160° C., 0.1 Torr) to recover 130.7 g (recovery rate 33.5 wt. %) of α-hydroxy fatty acid methyl ester (S13) as the main fraction and 259.3 g (recovery rate 66.5 wt. %) of ω-hydroxy fatty acid methyl ester as the residue.

<α-Hydroxy fatty acid methyl ester (S13)>
Color (GH)≦1, acid value=1.1, SV=180.1, OH value= 164.3, m.p.=33.6° C., unsaponifiable material=3.2 wt. %, odor=☉ , purity=81.0 wt. %.

<ω-Hydroxy fatty acid methyl ester (S14)>
Color (GH)≧18, acid value=2.5, SV=119.8, OH value=68.1, m.p.=50.8° C.

Example 8

The ω-hydroxy fatty acid methyl ester obtained as the residue in Example 7, 200 g, was subjected to vacuum distillation (200° C., 0.1 Torr) to recover 14.6 g (recovery rate 7.3 wt. %) of α-hydroxy fatty acid methyl ester (S15) as the main fraction and 185.4 g of residue.

<ω-Hydroxy fatty acid methyl ester (S15)>
Color (GH)=11, acid value=0.8, SV=120.0, OH value=90.3, m.p.=80.4° C., odor=☉, purity=52.4 wt. %.

Example 9

To the lanolin fatty acid methyl ester (OH value=64.0) (350 g) from which ω-hydroxy fatty acids had been removed as a solid fraction by solvent fractionation using petroleum ether was added 15.3 g of boric anhydride and the reaction was carried out at 100° C. for 2 hours. The reaction product, 344.5 g, was then subjected to vacuum distillation (190° C., 0.005 Torr) to recover 175.4 g (recovery rate 50.9 wt. %) of a non-hydroxy fatty acid methyl ester fraction as the distillate and 169.1 g (recovery rate 49.1 wt. %) of a hydroxy fatty acid methyl ester fraction as the residue. These fractions were respectively purified as in Example 1 to provide the following non-hydroxy fatty acid methyl ester (S16) and hydroxy fatty acid methyl ester (S17).

<Non-hydroxy fatty acid methyl ester (S16)>
Color (GH)=1, acid value=0.3, SV=178.0, OH value=8.5, m.p.=31.3° C. (m.p. in free form=49.8° C.), unsaponifiable material=0.8 wt. %, odor=☉, purity=90.2 wt. %, hydroxy fatty acid content=1.6 wt. %.

<Hydroxy fatty acid methyl ester (S17)>
Color (GH)≧18, acid value=2.1, SV=152.0, OH value= 112.3, m.p.=41.8° C.

Example 10

The boric acid ester of hydroxy fatty acid methyl ester obtained as the distillation residue in Example 9 (160 g) was dissolved in 120 ml of methyl ethyl ketone at elevated temperature and the solution was washed with 4 portions of 60 ml each of lukewarm water to hydrolytically remove the boric acid. The methyl ethyl ketone was then removed to provide 128 g of hydroxy fatty acid methyl ester (OH value=102.3).

This hydroxy fatty acid methyl ester was subjected to vacuum distillation (160° C., 0.1 Torr) to recover 45.0 g (recovery rate 35.2 wt. %) of α-hydroxy fatty acid methyl ester (S18) as the main distillate and 83.0 g of residue.

<α-Hydroxy fatty acid methyl ester (S18)>
Color (GH)≦1, acid value=0.5, OH value=163.9, m.p.= 34.1° C., odor=☉, purity=80.6 wt. %.

Example 11

The non-hydroxy fatty acid methyl ester obtained in Example 2, the α-hydroxy fatty acid methyl ester obtained in Example 7 and the ω-hydroxy fatty acid methyl ester obtained in Example 8 were respectively hydrolyzed with an aqueous solution of sodium hydroxide to provide a non-hydroxy fatty acid fraction, an α-hydroxy fatty acid fraction and an ω-hydroxy fatty acid fraction, respectively. The analytical data on each fraction are presented below.

<Non-hydroxy fatty acid (S19)>
Color (GH)≧1, acid value=177.8, SV=188.3, OH value= 11.0, m.p.=48.9° C., purity=92.0 wt. %, hydroxy fatty acid content=2.4 wt. %.

<α-Hydroxy fatty acid (S20)>
Color (GH)=3, acid value=171.3, OH value=151.9, m.p.= 79.6° C., transparent melting point=75.4° C., saponification value=183.6.

<ω-Hydroxy fatty acid (S21)>
Color (GH)=9, acid value=110.5, OH value=101.5, m.p.= 115.8° C.

Example 12

A lanolin fatty acid with a melting point of 54.9° C. was methylated to give a starting methyl ester with an acid value of 0.6, a saponification value of 165.3, a hydroxyl value of 44.2, an unsaponifiable material of 1.8% and a color (GH) value of 14. To 18.7 kg of this starting methyl ester was added 0.62 kg of boric acid to prepare the boric acid ester as in Example 1. This ester was subjected to vacuum distillation (190° C., 0.05 Torr) to provide 53% of a non-hydroxy fatty acid methyl ester fraction and, as the residue, 8.8 kg (47%) of a hydroxy fatty acid methyl ester fraction. The latter boric acid ester was hydrolyzed to remove boric acid to provide a hydroxy fatty acid methyl ester fraction with a color (GH) value of ≧18, an acid value of 1.3, a hydroxyl value of 78.1 and a melting point of 56.9° C.

This hydroxy fatty acid methyl ester, 5.5 kg, was subjected to vacuum distillation (160° C., 0.05 Torr) to recover 1.4 kg of α-hydroxy fatty acid methyl ester. This fraction was further hydrolyzed as in Example 11 to provide the following α-hydroxy fatty acid (S22).

<α-Hydroxy fatty acid (S22)>
Color (GH)=4–, acid value=184.2, OH value=169.4, saponification value=174.6, m.p.=70.3° C., transparent m.p.=76.5° C., unsaponifiable material=1.4 wt. %, purify=82.8 wt. %.

Example 13

Using 105 kg of the same starting material as used in Example 12 and 2.7 kg of boric acid, the procedure of Example 1 was otherwise repeated to prepare the boric acid ester. This ester was subjected to vacuum distillation (170° C., 0.05 Torr) to provide a non-hydroxy fatty acid methyl ester fraction 1 (38.0%) and a residue fraction 1.

The above residue fraction 1 was further subjected to vacuum distillation (195° C., 0.01 Torr) to recover a non-hydroxy fatty acid methyl ester fraction 2 (16.9%) and a residue fraction 2 (43.0%).

The boric acid ester residue fraction 2 was hydrolyzed to remove boric acid and thereby provide 45.9 kg of hydroxy fatty acid methyl ester. This hydroxy fatty acid methyl ester was subjected to vacuum distillation (160° C., 0.03 Torr) to recover α-hydroxy fatty acid methyl ester with a color (GH) value of 1+, an acid value of 0.2, a hydroxyl value of 162.9 and a melting point of 63.9° C.

This product was hydrolyzed as in Example 11 to give the following α-hydroxy fatty acid (S23).

<α-Hydroxy fatty acid (S23)>
Color (GH)=3+, acid value=179.9, OH value=175.9, saponification value=190.6, m.p.=63.9° C., transparent m.p.=78.6° C., unsaponifiable material=1.2 wt. %.

The composition of each of the fatty acid fractions obtained in the above examples was analyzed by gas chromatography. The results are shown in Tables 2–5.

TABLE 2

| Example No. | EX. 1 | EX. 3 | EX. 4 | EX. 5 |
|---|---|---|---|---|
| Sample code | S1 | S5 | S7 | S9 |
| Distillation temperature (°C.) | 170 | 170 | 140 | 170 |
| Distillation pressure (Torr) | 0.1 | 0.1 | 0.5 | 0.1 |
| Distillation yield (wt. %) | 39.9 | 39.6 | 39.4 | 39.0 |
| Non-hydroxy fraction | | | | |
| n-$C_{12}$–$C_{30}$ (even number) | 18.1 | 18.0 | 17.8 | 17.5 |
| n-$C_{15}$–$C_{19}$ (odd number) | 1.6 | 1.5 | 1.2 | 1.0 |
| iso-$C_{12}$–$C_{30}$ | 35.1 | 34.5 | 32.6 | 32.1 |
| anteiso-$C_{11}$–$C_{31}$ | 35.5 | 36.2 | 38.3 | 38.5 |
| Sub total | 90.3 | 90.2 | 89.9 | 89.1 |
| Hydroxy fatty acid fraction | | | | |
| n-$C_{14}$–$C_{20}$ (even number) | 0.8 | 1.0 | 1.3 | 1.4 |
| n-$C_{15}$–$C_{17}$ (odd number) | — | — | — | — |
| iso-$C_{14}$–$C_{24}$ | 0.1 | 0.1 | 0.3 | 0.3 |
| anteiso-$C_{15}$–$C_{25}$ | — | — | — | — |
| Sub total | 0.9 | 1.1 | 1.6 | 1.7 |
| Others | 8.8 | 8.7 | 8.5 | 9.2 |

TABLE 3

| Example No. | EX. 6 | EX. 7 | EX. 9 | EX. 10 |
|---|---|---|---|---|
| Sample code | S11 | S13 | S16 | S18 |
| Distillation temperature (°C.) | 170 | 160 | 190 | 160 |
| Distillation pressure (Torr) | 0.02 | 0.1 | 0.005 | 0.1 |
| Distillation yield (wt. %) | 24.3 | 33.5 | 50.9 | 35.2 |
| Non-hydroxy fraction | | | | |
| n-$C_{12}$–$C_{30}$ (even number) | 18.6 | 2.4 | 17.8 | 2.5 |
| n-$C_{15}$–$C_{19}$ (odd number) | 1.6 | — | 1.1 | — |
| iso-$C_{12}$–$C_{30}$ | 34.2 | 4.7 | 33.2 | 4.2 |
| anteiso-$C_{11}$–$C_{31}$ | 35.0 | 5.3 | 37.9 | 5.8 |
| Sub total | 89.4 | 12.4 | 90.2 | 12.5 |
| Hydroxy fatty acid fraction | | | | |
| n-$C_{14}$–$C_{20}$ (even number) | 2.4 | 58.1 | 1.9 | 57.8 |
| n-$C_{15}$–$C_{17}$ (odd number) | — | 3.5 | — | 3.5 |
| iso-$C_{14}$–$C_{24}$ | — | 16.9 | 0.4 | 17.0 |
| anteiso-$C_{15}$–$C_{25}$ | — | 2.6 | — | 2.3 |
| Sub total | 2.4 | 81.0 | 2.3 | 80.6 |
| Others | 8.2 | 6.6 | 7.5 | 6.9 |

TABLE 4

| Example No. | EX. 12 | EX. 13 |
|---|---|---|
| Sample code | S22 | S23 |
| Non-hydroxy fraction | | |
| n-$C_{12}$–$C_{30}$ (odd number) | 3.5 | 3.0 |
| iso-$C_{12}$–$C_{30}$ | 3.9 | 2.7 |
| anteiso-$C_{11}$–$C_{31}$ | 3.4 | 3.5 |
| Hydroxy fatty acid fraction | | |
| n-$C_{14}$–$C_{20}$ (even number) | 54.6 | 55.9 |
| n-$C_{15}$–$C_{17}$ (odd number) | 3.2 | 3.2 |
| iso-$C_{14}$–$C_{24}$ | 22.1 | 21.8 |
| anteiso-$C_{15}$–$C_{25}$ | 3.0 | 3.3 |
| Others | 6.3 | 6.6 |

TABLE 5

| Example No. | EX. 8 |
| --- | --- |
| Sample code | S15 |
| Distillation temperature (°C.) | 200 |
| Distillation pressure (Torr) | 0.1 |
| Distillation yield (wt. %) | 7.3 |
| Hydroxy fatty acid fraction | |
| Normal | |
| ω-C28 | 17.0 |
| ω-C30 | 29.4 |
| ω-C32 | 3.4 |
| ω-C34 | 2.6 |
| Total | 52.4 |
| Others | 47.6 |

The cosmetic products prepared using the above-obtained non-hydroxy fatty acid fractions, hydroxy fatty acid fractions and their salts of the invention are shown in the following Examples 14–35.

Examples 14–19 and Comparative Examples 1–6

As shown below in Tables 6–8, vanishing creams, emollient (nutritive) lotions and emollient (nutritive) creams (Ex. 14–19) were prepared using S9 and S10 of Example 5 and S19, S20 and S21 of Example 11.

Using stearic acid, lanolin fatty acid and their esters in lieu of the above samples, control skin-care cosmetics (REF 1–6) were prepared in otherwise the same manner.

In the tables presented below, the following abbreviations are used to denote various ingredients.

SA: Stearic acid, LF: Lanolin fatty acid,

SALC: Stearyl alcohol, SABt: Butyl stearate,

LFIPA: Lanolin fatty acid isopropyl ester,

GLYMSA: Glycerol monostearate,

TCP: Tocopherol acetate, POBZ: p-Hydroxybenzoic ester

GLY: Glycerol, PG: Propylene glycol,

KOH: Potassium hydroxide,

MOEO10: Polyoxyethylene(10) monooleate,

PGMSA: Propylene glycol monostearate,

EOCE10: Polyoxyethylene(10) cetyl ether,

PAIPA: Isopropyl palmitate, AAGA: Lanolin acetate,

MCWAX: Microcrystalline wax, CANWAX: Candelilla wax,

Tio: Titanium oxide, PIG: Inorganic pigment,

CSALC: Cetostearyl alcohol, LL: Liquid lanolin,

CMC: Carboxymethylcellulose sodium,

ODL: Octyl dodecanol, MYIPA: Isopropyl myristate,

CAWAX: Carnauba wax, MCWAX: Microcrystalline wax,

R201: Red 201, R202: Red 202,

YAI: Yellow aluminum chelate, R223: Red 223,

EtOH95: 95% Ethanol, ISA: Isostearic acid, l-Mnt: L-Menthol, EOPODTD: Polyoxyethylene(12)-polyoxypropylene(6) decyl tetradecyl ether, DL-TCP: dl-α-Tocopherol, 13BG: 1,3-Butylene glycol, EOCO20: Polyoxyethylene(20) sesquioleate, ABGDO: Avogado oil, TGLY: Tallow fatty acid triglyceride, pWAX: Paraffin wax, Si: Silicone oil, EOBA20: Polyoxyethylene(20) behenyl ether, EOTOAS60: Polyoxyethylene(60) sorbitol tetraoleate, EOLHSTEA: Polyoxyethylene(3) triethanolamine lauryl sulfate (40%), LHSNa: Sodium lauryl sulfate (30%), LDEAD: Lauroyl diethanolamide, DSAPEG: Polyethylene glycol distearate, LA: Lanolin alcohol, P70: Liquid paraffin, MOEO: Polyoxyethylene monooleate, TEA: Triethanolamine, CHO: Cholesterol, ODL: Soft lanolin fatty acid octyldodecyl, TCP: d-α-tocopherol acetate, MSEOS: Polyoxyethylene sorbitan monostearate (EO20), OALC: Oleyl alcohol, CLEH: High-melting lanolin fatty acid cholesterol ester, LEEO3: Polyoxyethylene lauryl ether (3 EO), LEEO23: Polyoxyethylene lauryl ether (23 EO), LDEAM: Lauric diethanolamide, BEALC: Behenyl alcohol, TOEOS: Polyoxyethylene(40) sorbitol tetraoleate, BHT: Antioxidant, BG: 1,3-Butylene glycol, PAB: Preservative/antimicrobial agent, CEALC: Cetyl alcohol, SS6.5: Sucrose stearate (HLB= 6.5), HYECE: Hydroxyethylcellulose, LHSAM: Ammonium lauryl sulfate, LADBE: Coconut oil fatty acid amine propyl betaine, PPG5:PPG5 Ceteth 10 phosphate, PROTE: Animal protein hydrolysate.

TABLE 6

| Ingredient | | EX. 14 | EX. 15 | REF. 1 | REF. 2 |
| --- | --- | --- | --- | --- | --- |
| A | SA | — | — | 10.0 | — |
| | LF | — | — | — | 10.0 |
| | S19 | — | 2.0 | — | — |
| | S20 | 10.0 | 8.0 | — | — |
| | SALC | 4.0 | 4.0 | 4.0 | 4.0 |
| | SABt | — | — | 8.0 | — |
| | LFIPA | — | — | — | 8.0 |
| | S9 | 8.0 | 1.0 | — | — |
| | S10 | — | 7.0 | — | — |
| | GLYMSA | 2.0 | 2.0 | 2.0 | 2.0 |
| | TCP | 0.2 | 0.2 | 0.2 | 0.2 |
| | POBZ | 0.1 | 0.1 | 0.1 | 0.1 |
| B | GLY | 4.0 | 4.0 | 4.0 | 4.0 |
| | PG | 10.0 | 10.0 | 10.0 | 10.0 |
| | KOH | 0.4 | 0.4 | 0.4 | 0.4 |
| | Purified-water | 61.3 | 61.3 | 61.3 | 61.3 |
| Total | | 100.0 | 100.0 | 100.0 | 100.0 |

Production process: The above A and B ingredients were respectively blended and heated to 70° C. and B was gradually added to A with stirring. The stirring was continued for a while, after which the mixture was well homogenized with a homomixer. The emulsion was then allowed to cool to room temperature under agitation.

TABLE 7

| Ingredient | | EX. 16 | EX. 17 | REF. 3 | REF. 4 |
| --- | --- | --- | --- | --- | --- |
| A | SA | — | — | 0.2 | — |
| | LF | — | — | — | 0.2 |
| | S19 | — | 0.1 | — | — |
| | S21 | 0.2 | 0.1 | — | — |
| | Cetanol | 1.5 | 1.5 | 1.5 | 1.5 |

TABLE 7-continued

| Ingredient | | EX. 16 | EX. 17 | REF. 3 | REF. 4 |
|---|---|---|---|---|---|
| | Petrolatum | 3.0 | 3.0 | 3.0 | 3.0 |
| | LA | 2.0 | 2.0 | 2.0 | 2.0 |
| | P70 | 10.0 | 10.0 | 10.0 | 10.0 |
| | MOEO10 | 2.0 | 2.0 | 2.0 | 2.0 |
| | TCP | 0.2 | 0.2 | 0.2 | 0.2 |
| | POBZ | 0.1 | 0.1 | 0.1 | 0.1 |
| B | GLY | 3.0 | 3.0 | 3.0 | 3.0 |
| | PG | 5.0 | 5.0 | 5.0 | 5.0 |
| | TEA | 1.0 | 1.0 | 1.0 | 1.0 |
| | Purified-water | 72.0 | 72.0 | 72.0 | 72.0 |
| Total | | 100.0 | 100.0 | 100.0 | 100.0 |

Production process: The same as above.

TABLE 8

| Ingredient | | EX. 18 | EX. 19 | REF. 5 | REF. 6 |
|---|---|---|---|---|---|
| A | Beeswax | 2.0 | 2.0 | 2.0 | 2.0 |
| | SALC | 5.0 | 5.0 | 5.0 | 5.0 |
| | SA | — | — | 8.0 | — |
| | LF | — | — | — | 8.0 |
| | S19 | — | 3.0 | — | — |
| | S20 | 8.0 | 5.0 | — | — |
| | Squalene | 10.0 | 10.0 | 10.0 | 10.0 |
| | PGMSA | 3.0 | 3.0 | 3.0 | 3.0 |
| | EOCE10 | 1.0 | 1.0 | 1.0 | 1.0 |
| | TCP | 0.2 | 0.2 | 0.2 | 0.2 |
| | POBZ | 0.1 | 0.1 | 0.1 | 0.1 |
| | GLY | 4.0 | 4.0 | 4.0 | 4.0 |
| B | PG | 8.0 | 8.0 | 8.0 | 8.0 |
| | TEA | 1.0 | 1.0 | 1.0 | 1.0 |
| | Purified water | 57.7 | 57.7 | 57.7 | 57.7 |
| Total | | 100.0 | 100.0 | 100.0 | 100.0 |

Production process: The same as above.

Ten female testers (aged 19–55 years) were instructed to use the vanishing creams (1), emollient lotions (2) and emollient creams (3) prepared as above and interviewed for texture, spreadability on the skin and the feeling of use. The results are shown in Table 9.

TABLE 9

| | Texture | | Spreadability | | Feeling of use | |
|---|---|---|---|---|---|---|
| | Good | Not good | Good | Not good | Good | Not good |
| EX. 14 | 9 | 1 | 8 | 2 | 10 | 0 |
| EX. 15 | 9 | 1 | 9 | 1 | 10 | 0 |
| REF. 1 | 1 | 9 | 2 | 8 | 0 | 10 |
| REF. 2 | 5 | 5 | 6 | 4 | 5 | 5 |
| EX. 16 | 8 | 2 | 7 | 3 | 7 | 3 |
| EX. 17 | 8 | 2 | 7 | 3 | 8 | 2 |
| REF. 3 | 2 | 8 | 3 | 7 | 3 | 7 |
| REF. 4 | 4 | 6 | 5 | 5 | 4 | 6 |
| EX. 18 | 9 | 1 | 8 | 2 | 9 | 1 |
| EX. 19 | 10 | 0 | 9 | 1 | 10 | 0 |
| REF. 5 | 1 | 9 | 2 | 8 | 1 | 9 |
| REF. 6 | 3 | 7 | 5 | 5 | 4 | 6 |

Examples 20–25 and Comparative Examples 7–12

As shown below in Tables 10–12, makeup products, namely foundation (oleaginous ointment type, lotion type) and rouge (stick type) were prepared using S7 and S8 of Example 4, S9 and S10 of Example 5 and S19 and S20 of Example 11 (EX. 20–25). In addition, control makeup products (REF. 7–12) were prepared using palmitic acid, stearic acid, myristic acid, lanolin fatty acid, their esters, castor oil, etc. in lieu of the above samples.

TABLE 10

| Ingredient | EX. 20 | EX. 21 | REF. 7 | REF. 8 |
|---|---|---|---|---|
| Base | | | | |
| P70 | 24.2 | 24.2 | 24.2 | 24.2 |
| PAIPA | — | — | 15.0 | — |
| LFIPA | — | — | — | 15.0 |
| S7 | 15.0 | 5.0 | — | — |
| S8 | — | 10.0 | — | — |
| Cetanol | 2.0 | 2.0 | 2.0 | 2.0 |
| AAGA | 3.0 | 3.0 | 3.0 | 3.0 |
| MCWAX | 7.0 | 7.0 | 7.0 | 7.0 |
| Ozocerite | 8.0 | 8.0 | 8.0 | 8.0 |
| CAWAX | 0.5 | 0.5 | 0.5 | 0.5 |
| TCP | 0.2 | 0.2 | 0.2 | 0.2 |
| POBZ | 0.1 | 0.1 | 0.1 | 0.1 |
| Color | | | | |
| TiO | 15.0 | 15.0 | 15.0 | 15.0 |
| Kaolin | 15.0 | 15.0 | 15.0 | 15.0 |
| Talc | 6.0 | 6.0 | 6.0 | 6.0 |
| PIG | 4.0 | 4.0 | 4.0 | 4.0 |
| Total | 100.0 | 100.0 | 100.0 | 100.0 |

Production process: The color ingredients were admixed. Separately, the base ingredients were blended and melted to uniform consistency by heating. The color mix was added to the molten base mix and the composition was kneaded through a roll mill. After color adjustment, the composition was cooled under agitation, cast in a container and allowed to cool.

TABLE 11

| Ingredient | EX. 22 | EX. 23 | REF. 9 | REF. 10 |
|---|---|---|---|---|
| Base A | | | | |
| SA | — | — | 2.4 | — |
| LF | — | — | — | 2.4 |
| S19 | — | 1.2 | — | — |
| S20 | 2.4 | 1.2 | — | — |
| PGMSA | 2.0 | 2.0 | 2.0 | 2.0 |
| CSALC | 0.2 | 0.2 | 0.2 | 0.2 |
| LL | 2.0 | 2.0 | 2.0 | 2.0 |
| P70 | 3.0 | 3.0 | 3.0 | 3.0 |
| MAIPA | — | — | 8.5 | — |
| LFIPA | — | — | — | 8.5 |
| S7 | — | 4.0 | — | — |
| S8 | 8.5 | 4.5 | — | — |
| TCP | 0.2 | 0.2 | 0.2 | 0.2 |
| POBZ | 0.1 | 0.1 | 0.1 | 0.1 |
| Base B | | | | |
| CMC | 0.2 | 0.2 | 0.2 | 0.2 |
| Bentnite | 0.5 | 0.5 | 0.5 | 0.5 |
| PG | 4.0 | 4.0 | 4.0 | 4.0 |
| TEA | 1.1 | 1.1 | 1.1 | 1.1 |
| Purified water | 63.8 | 63.8 | 63.8 | 63.8 |
| Color | | | | |
| TiO | 8.0 | 8.0 | 8.0 | 8.0 |
| Talc | 4.0 | 4.0 | 4.0 | 4.0 |
| PIG | q.s. | q.s. | q.s. | q.s. |
| Total | 100.0 | 100.0 | 100.0 | 100.0 |

Production process: The steps 1–5 described below were followed.

1. The color materials were mixed well and pulverized.

2. Separately, base A ingredients were blended and melted by heating.

3. To prepare base B, purified water was warmed to 70° C. and bentonite was added. Then, a dispersion of carboxymethylcellulose Na in propylene glycol was added and dissolved, followed by addition of triethanolamine.

4. The color mix 1 was added to the base B mix with stirring. After completion of addition, the mixture was subjected to colloid mill processing.

5. The color dispersion 4 was heated to 75° C. and the base A mix 2 to 80° C. and 2 was added to 4 under constant stirring. The stirring was continued until the composition had cooled to room temperature.

TABLE 12

| Ingredient | EX. 24 | EX. 25 | REF. 11 | REF. 12 |
|---|---|---|---|---|
| Base |  |  |  |  |
| Castor oil | — | — | 40.6 | 40.6 |
| S9 | — | 10.0 | — | — |
| S10 | 40.6 | 30.6 | — | — |
| Beeswax | 5.0 | 5.0 | 5.0 | 5.0 |
| Lanolin | 5.0 | 5.0 | 5.0 | 5.0 |
| ODL | 15.0 | 15.0 | 15.0 | 15.0 |
| MYIPA | — | — | 10.0 | — |
| LFIPA | — | — | — | 10.0 |
| S7 | 10.0 | 6.0 | — | — |
| S8 | 10.0 | 4.0 | — | — |
| CANWAX | 7.0 | 7.0 | 7.0 | 7.0 |
| CAWAX | 2.0 | 2.0 | 2.0 | 2.0 |
| Ozocerite | 4.0 | 4.0 | 4.0 | 4.0 |
| MCWAX | 6.0 | 6.0 | 6.0 | 6.0 |
| TCP | 0.2 | 0.2 | 0.2 | 0.2 |
| POBZ | 0.1 | 0.1 | 0.1 | 0.1 |
| Color |  |  |  |  |
| TiO | 1.0 | 1.0 | 1.0 | 1.0 |
| R201 | 1.0 | 1.0 | 1.0 | 1.0 |
| R202 | 2.0 | 2.0 | 2.0 | 2.0 |
| YA1 | 1.0 | 1.0 | 1.0 | 1.0 |
| R223 | 0.1 | 0.1 | 0.1 | 0.1 |
| Total | 100.0 | 100.0 | 100.0 | 100.0 |

Production process: The base ingredients were blended and melted to uniform consistency by heating. To this mix was added the color ingredients and the mixture was evenly dispersed using a roll mill. The composition was subjected to re-melting, defoamed, cast into a container and quenched to solidity. The oleaginous ointment type foundations (1), lotion type foundations (2) and lipsticks (3) were tested in the same manner as the skin cosmetics. The results are set forth in Table 13.

TABLE 13

|  | Consistency | | Spreadability | | Degree of satisfaction | |
|---|---|---|---|---|---|---|
|  | Good | Not good | Good | Not good | Good | Not good |
| EX. 20 | 8 | 2 | 10 | 0 | 9 | 1 |
| EX. 21 | 9 | 1 | 10 | 0 | 10 | 0 |
| REF. 7 | 2 | 8 | 1 | 9 | 1 | 9 |
| REF. 8 | 5 | 5 | 5 | 5 | 5 | 5 |
| EX. 22 | 10 | 0 | 9 | 1 | 9 | 1 |
| EX. 23 | 10 | 0 | 9 | 1 | 10 | 0 |
| REF. 9 | 1 | 9 | 1 | 9 | 1 | 9 |
| REF. 10 | 4 | 6 | 4 | 6 | 4 | 6 |
| EX. 24 | 8 | 2 | 8 | 2 | 9 | 1 |
| EX. 25 | 9 | 1 | 9 | 1 | 10 | 0 |

TABLE 13-continued

|  | Consistency | | Spreadability | | Degree of satisfaction | |
|---|---|---|---|---|---|---|
|  | Good | Not good | Good | Not good | Good | Not good |
| REF. 11 | 2 | 8 | 2 | 8 | 1 | 9 |
| REF. 12 | 5 | 5 | 4 | 6 | 4 | 6 |

Examples 26–33 and Comparative Examples 13–20

As shown in Tables 14–17, the hair-care products, namely hair tonics, hair lotions, hair creams and liquid cream shampoos (EX. 26–33) were prepared using S5 and S6 of Example 3, S7 and S8 of example 4 and S19, S20 and S21 of Example 11. In addition, control hair-care products (REF. 13–20) were prepared using palmitic acid, stearic acid, isostearic acid, lanolin fatty acid, their esters, tallow fatty acid triglyceride, castor oil, etc. in lieu of the above samples.

TABLE 14

| Ingredient | EX. 26 | EX. 27 | REF. 13 | REF. 14 |
|---|---|---|---|---|
| EtOH95 | 70.0 | 70.0 | 70.0 | 70.0 |
| Castor oil | — | — | 1.0 | — |
| LFIPA | — | — | — | 1.0 |
| S5 | — | 0.5 | — | — |
| S6 | 1.0 | 0.5 | — | — |
| ISA | — | — | 0.1 | — |
| LF | — | — | — | 0.1 |
| S19 | — | 0.1 | — | — |
| S20 | 0.1 | — | — | — |
| 1-Mnt | 0.1 | 0.1 | 0.1 | 0.1 |
| EOPODTD | 1.0 | 1.0 | 1.0 | 1.0 |
| DL-TCP | 0.2 | 0.2 | 0.2 | 0.2 |
| 13BG | 3.0 | 3.0 | 3.0 | 3.0 |
| POBZ | 0.1 | 0.1 | 0.1 | 0.1 |
| Purified water | 24.6 | 24.6 | 24.6 | 24.6 |
| Total | 100.0 | 100.0 | 100.0 | 100.0 |

Production process: The ethanol-soluble ingredients and the water-soluble ingredients were respectively dissolved well with stirring and the aqueous solution was added to the ethanol solution. The resultant homogeneous composition was filtered to provide a finished product.

TABLE 15

| Ingredient | EX. 28 | EX. 29 | REF. 15 | REF. 16 |
|---|---|---|---|---|
| Castor oil | — | — | 1.0 | — |
| LFIPA | — | — | — | 1.0 |
| S9 | — | 0.5 | — | — |
| S10 | 1.0 | 0.5 | — | — |
| SA | — | — | 4.0 | — |
| LF | — | — | — | 4.0 |
| S19 | 1.5 | — | — | — |
| S20 | 2.5 | 3.0 | — | — |
| S21 | — | 1.0 | — | — |
| Cetanol | 0.5 | 0.5 | 0.5 | 0.5 |
| EOCO20 | 1.0 | 1.0 | 1.0 | 1.0 |
| DL-TCP | 0.1 | 0.1 | 0.1 | 0.1 |
| GLY | 5.0 | 5.0 | 5.0 | 5.0 |
| POBZ | 0.1 | 0.1 | 0.1 | 0.1 |
| EtOH95 | 10.0 | 10.0 | 10.0 | 10.0 |
| Purified water | 78.3 | 78.3 | 78.3 | 78.3 |
| Total | 100.0 | 100.0 | 100.0 | 100.0 |

Production process: The same as above.

TABLE 16

| Ingredient | | EX. 30 | EX. 31 | REF. 17 | REF. 18 |
|---|---|---|---|---|---|
| A | SA | — | — | 4.0 | — |
| | LF | — | — | — | 4.0 |
| | S19 | 4.0 | 0.8 | — | — |
| | S20 | — | 2.8 | — | — |
| | S21 | — | 0.4 | — | — |
| | Cetanol | 3.0 | 3.0 | 3.0 | 3.0 |
| | P70 | 25.0 | 25.0 | 25.0 | 25.0 |
| | PWAX | 4.0 | 4.0 | 4.0 | 4.0 |
| | ABGDO | 5.0 | 5.0 | 5.0 | 5.0 |
| | TGLY | — | — | 10.0 | — |
| | LFIPA | — | — | — | 10.0 |
| | S5 | 10.0 | 2.0 | — | — |
| | S6 | — | 0.8 | — | — |
| | Si | 0.2 | 0.2 | 0.2 | 0.2 |
| | EOBA20 | 1.5 | 1.5 | 1.5 | 1.5 |
| | EOTOAS60 | 1.0 | 1.0 | 1.0 | 1.0 |
| | GLMSA | 1.5 | 1.5 | 1.5 | 1.5 |
| | TCP | 0.2 | 0.2 | 0.2 | 0.2 |
| | POBZ | 0.1 | 0.1 | 0.1 | 0.1 |
| B | 13BG | 5.0 | 5.0 | 5.0 | 5.0 |
| | Purified water | 39.5 | 39.5 | 39.5 | 39.5 |
| Total | | 100.0 | 100.0 | 100.0 | 100.0 |

Production process: The A ingredients were blended and melted by heating at 80° C. Separately, B was heated to about 85° C. Then, A was added to B under constant stirring and the resultant composition was allowed to cool to room temperature.

TABLE 17

| Ingredient | EX. 32 | EX. 33 | REF. 19 | REF. 20 |
|---|---|---|---|---|
| PAIPA | — | — | 1.0 | — |
| LFIPA | — | — | — | 1.0 |
| S7 | 1.0 | 0.2 | — | — |
| S8 | — | 0.8 | — | — |
| EOLHSTEA | 0.0 | 30.0 | 30.0 | 30.0 |
| LHSNa | 15.0 | 15.0 | 15.0 | 15.0 |
| LDEAD | 3.0 | 3.0 | 3.0 | 3.0 |
| DSAPEG | 2.0 | 2.0 | 2.0 | 2.0 |
| TCP | 0.2 | 0.2 | 0.2 | 0.2 |
| POBZ | 0.2 | 0.2 | 0.2 | 0.2 |
| Purified water | 48.6 | 48.6 | 48.6 | 48.6 |
| Total | 100.0 | 100.0 | 100.0 | 100.0 |

Production process: The above ingredients were evenly melted by heating at 70°–80° C. and allowed to cool to room temperature with constant stirring.

Ten female (aged 19–55 years) and 10 male (aged 20–65 years) panelists were instructed to use-test the hair tonics (1), hair lotions (2), hair creams (3) and liquid cream shampoos. The results are set forth in Table 18.

TABLE 18

| | Hair sheen | | Manageability | | Feeling of use | |
|---|---|---|---|---|---|---|
| | Good | Not good | Good | Not good | Good | Not good |
| EX. 26 | 16 | 4 | 16 | 4 | 16 | 4 |
| EX. 27 | 14 | 6 | 14 | 6 | 14 | 6 |
| REF. 13 | 8 | 12 | 8 | 12 | 8 | 12 |
| REF. 14 | 6 | 14 | 6 | 14 | 6 | 14 |
| EX. 28 | 19 | 1 | 18 | 2 | 18 | 2 |
| EX. 29 | 19 | 1 | 18 | 2 | 18 | 2 |
| REF. 15 | 8 | 12 | 8 | 12 | 8 | 12 |
| REF. 16 | 9 | 11 | 8 | 12 | 10 | 10 |

TABLE 18-continued

| | Hair sheen | | Manageability | | Feeling of use | |
|---|---|---|---|---|---|---|
| | Good | Not good | Good | Not good | Good | Not good |
| EX. 30 | 9 | 1 | 19 | 1 | 19 | 1 |
| EX. 31 | 9 | 1 | 19 | 1 | 19 | 1 |
| REF. 17 | 2 | 18 | 1 | 19 | 1 | 19 |
| REF. 18 | 8 | 12 | 6 | 14 | 8 | 12 |
| EX. 32 | 17 | 3 | 16 | 4 | 17 | 3 |
| EX. 33 | 16 | 4 | 16 | 4 | 18 | 2 |
| REF. 19 | 4 | 16 | 4 | 16 | 4 | 16 |
| REF. 20 | 10 | 10 | 8 | 12 | 10 | 10 |

Example 34

In this example, an emulsion type mascara was prepared using non-hydroxy fatty acid fraction(S11). The formula is shown in Table 19.

TABLE 19

| Ingredient | | Amount |
|---|---|---|
| A | Non-hydroxy fatty acid (S11) | 5.0 |
| | P70 | 5.0 |
| | Beeswax | 3.0 |
| | Cetanol | 2.0 |
| | Carbon black | 2.0 |
| B | LHSNa | 0.3 |
| | PG | 3.0 |
| | Hydroxyethyl cellulose | 0.2 |
| | PAB | Trace |
| | Perfume | Trace |
| | Purified water | q.s. |

Production process: The A and B ingredients were respectively heated and evenly admixed. Then, A was added to B, and after thorough mixing, the composition was cooled to provide an emulsion-type mascara. A similar emulsion type mascara can be obtained by using α-hydroxy fatty acid (S23) in lieu of non-hydroxy fatty acid (S11).

Example 35

In this example, an oil type bath preparation was prepared using non-hydroxy fatty acid fraction (S19). The formula is shown in Table 20.

TABLE 20

| Ingredient | Amount |
|---|---|
| Non-hydroxy fatty acid (S19) | 10.0 |
| Olive oil | 10.0 |
| MYIPA | 5.0 |
| LDEAM | 3.0 |
| Perfume | Trace |
| PAB | Trace |
| P70 | q.s. |

Production process: The ingredients were evenly dissolved by heating and the composition was cooled to provide an oil type bath preparation. A similar oil type bath preparation can be obtained by using α-hydroxy fatty acid fraction (S23) in lieu of the above non-hydroxy fatty acid fraction (S19).

The following Test Examples 1–4 demonstrate that the α-hydroxy fatty acid fraction obtainable by the fractionation method of the invention has activity to promote keratinocyte proliferation and melanin production and is effective for prevention of hair graying, promotion of hair growth and antidandruff purposes.

Test Example 1

In this test example, the keratinocyte proliferation promoting effects of the non-hydroxy fatty acid (S19) and α-hydroxy fatty acid (S20) obtained in Example 11 and of the sodium and ammonium salts of S20 were investigated.

Cultured cells:

As the keratinocyte, SV40 transformed human keratinocyte which is an established cultured cell line was used.

Method:

In a clean bench, a culture medium composed of 2.5 ml of sterilized fetal calf serum, 75 ml of keratinocyte basal medium and 0.8 ml of antibiotic was seeded with $1.6 \times 10^5$ keratinocytes. The mixture was distributed in 3 ml aliquots into the wells of a 6-well plate and incubated in an atmosphere containing 5% $CO_2$ in a carbon dioxide incubator at 37° C. After 24 hours, the culture medium was removed and 1.5 ml of keratinocyte basal medium, 1.5 ml of Dulbecco's modified Eagle minimal essential medium, 5 µg of linolic acid and 100 µg/ml of fatty acid-free bovine serum albumin were added. Then, the test substance was added at a final concentration of 0.1 µg/ml or 1.0 µg/ml and the system was incubated for 1 week.

After completion of incubation, the medium was discarded and 0.02% EDTA and, then, Dulbecco's phosphate buffer containing 0.25% trypsin were added for digestive exfoliation of the cells. These reagents were then removed and 1 ml of Dulbecco's phosphate buffer was added to each well to prepare a suspension. The cell count was then determined using a hemocytometer.

Results:

The percent cell growth promoting effect of each test substance was evaluated with the cell growth rate of control (dosing concentration=0.0 µg/ml) being taken as 100. The results are shown in Table 21.

TABLE 21

| Test substance | Concentration of test substance (µg/ml) | | | |
| --- | --- | --- | --- | --- |
|  | 0.0 | 0.1 | 1.0 | 10.0 |
| S20 | 100 | 140 | 200 | 140 |
| S20-Na salt | 100 | 130 | 190 | 140 |
| S20-NH$_4$ salt | 100 | 150 | 205 | 130 |
| S19 | 100 | 150 | 110 | 120 |

It is clear from Table 21 that the non-hydroxy fatty acid (S19) raised the keratinocyte growth rate to 1.5 times even at a low concentration of 0.1 µg/ml and α-hydroxy fatty acid (S20) and its salts increased the keratinocyte growth to more than 2-fold at a concentration of 1.0 µg/ml, indicating their marked promoting action on cell proliferation.

Test Example 2

In this test example, the melanin production promoting effect of the non-hydroxy fatty acid fraction (S19) and α-hydroxy fatty acid fraction (S20) obtained in Example 11 was tested.

Cultured cell:

As the cell for the evaluation of melanin production effect, B16 mouse melanoma cell line was used.

Method:

B16 mouse melanoma cells were cultured in 10% fetal calf serum-Eagle's MEM containing each test substance for 3 days.

After completion of cultivation, the cells were exfoliated by trypsin digestion and the digest was centrifuged to obtain a pellet. The degree of melanin production was evaluated against control by the naked eye.

The results are shown in Table 22.
[Criteria]

TABLE 22

| Test substance | Concentration (µg/ml) | | | |
| --- | --- | --- | --- | --- |
|  | 1 | 10 | 25 | 50 |
| S19 | − | − | ± | + |
| S20 | − | + | + | + |

It is apparent from Table 22 that the non-hydroxy fatty acid (S19) promoted melanin production overtly at 50 µg/ml and the α-hydroxy fatty acid (S20) did so at 10 µg/ml and higher concentrations.

Test Example 3

In this test example, a hair tonic was prepared using the α-hydroxy fatty acid fraction (S20) obtained in Example 11 and its inhibitory effect on graying of hair was tested.

Method:

According to the formula shown in Table 23, the various ingredients were dissolved in 99% ethyl alcohol and the solution was filtered to provide a hair tonic sample.

A control hair tonic was prepared in the same manner except that the active ingredient α-hydroxy fatty acid (S20) was omitted.

TABLE 23

| Ingredient | Amount |
| --- | --- |
| S20 | 3.0 |
| PG | 3.0 |
| Polyoxyethylene-hydrogenated castor oil | 3.0 |
| Perfume | 0.1 |
| 99% Ethyl alcohol | Balance |

Method:

A panel of 20 male testers with gray hair (aged 35–55 years) were instructed to use the test hair tonic and control hair tonic on the lateral sides of the scalp by the half-head method twice a day (morning and evening) for 3 consecutive months. The condition of hair in each half of the scalp after application was compared with that before application to evaluate the prophylactic or ameliorating effect on gray hair. The results are shown in Table 24.

TABLE 24

| Scale | Score |
| --- | --- |
| Test product is better | 10 |
| Test product is slightly better | 8 |
| Not different | 2 |
| Control product is slightly better | 0 |
| Control product is better | 0 |

It is apparent from Table 24 that compared with the control product (composition free of active ingredient), the test product containing α-hydroxy fatty acid (S20) reduced the amount of gray hair, showing a marked inhibitory effect on the graying of hair.

Test Example 4

In this example, the hair growth promoting and antidandruff effects of the test and control hair tonics prepared in Test Example 3 were tested.

Method:

Twenty (20) male subjects with dandruff (aged 10–20 years) and 20 male patients with male pattern alopecia (aged 30–40 years) who complained of comparatively severe falling hair were instructed to use the test and control hair tonics prepared in Test Example 3 (10 per group) twice a day for 3 consecutive months and the symptomatic improvement rates were determined. The results are shown in Table 25 (dandruff cases) and Table 26 (male pattern alopecia cases).

TABLE 25

|  | Hair tonic A group | Hair Tonic B group |
|---|---|---|
| Dandruff markedly reduced | 6 | 0 |
| Dandruff fairly reduced | 2 | 0 |
| Dandruff slightly reduced | 2 | 1 |
| No change | 0 | 9 |
| Dandruff increased | 0 | 0 |

TABLE 26

|  | Hair tonic A group | Hair Tonic B group |
|---|---|---|
| Falling hair markedly reduced | 5 | 0 |
| Falling hair fairly reduced | 3 | 0 |
| Falling hair slightly reduced | 2 | 2 |
| No change | 0 | 7 |
| Falling hair increased | 0 | 1 |

It is apparent from Table 26 that the test hair tonic containing α-hydroxy fatty acid fraction (S20) had hair growth promoting and antidandruff effects.

In the following Examples 36–43, various hair cosmetic products containing the α-hydroxy fatty acid fractions (S20), (S22) and (S23) obtained in Examples 11–13 and their salts are shown by way of example.

Example 36

In this example, a hair tonic was prepared using S22 in lieu of S20 in Table 23.

Example 37

In this example, a hair cream was prepared using the ammonium salt of α-hydroxy fatty acid (S20). The formula is shown in Table 27.

TABLE 27

| | Ingredient | Amount |
|---|---|---|
| A | S20 ammonium salt | 5.0 |
| | Liquid paraffin | 10.0 |
| | Cetanol | 3.0 |
| | GLYMSA | 3.0 |
| B | PG | 10.0 |
| | Methyl p-hydroxybenzoate | 0.2 |
| | Purified water | Balance |

Production process: A and B were independently dissolved by heating and maintained at 80° C. Then, A was added to B with stirring and the resultant composition was cooled to provide a hair cream.

Example 38

In this example, a hair oil was prepared using α-hydroxy fatty acid fraction (S20). The formula is shown in Table 28.

TABLE 28

| Ingredient | Amount |
|---|---|
| S20 | 9.0 |
| Olive oil | 10.0 |
| Squalane | Balance |

Production process: In squalane were dissolved the other ingredients to provide a hair oil.

Example 39

In this example, a hair shampoo was prepared using the potassium salt of α-hydroxy fatty acid (S23). The formula is shown in Table 29.

TABLE 29

| Ingredient | Amount |
|---|---|
| S23 potassium salt | 2.0 |
| LHSNa | 15.0 |
| LDEAM | 6.0 |
| PG | 7.0 |
| DSAPEG | 2.0 |
| Sodium benzoate | 0.3 |
| Citric acid | 0.1 |
| Perfume | 0.5 |
| Purified water | Balance |

Production process: To purified water were added the other ingredients and the mixture was heated to maintain at 80° C. The resultant solution was cooled to provide a hair shampoo.

Example 40

In this example, a hair tonic for inhibiting gray hair was prepared using α-hydroxy fatty acid fraction (S20). The formula is shown in Table 30.

TABLE 30

| Ingredient | Amount |
|---|---|
| S20 | 3.0 |
| Ethyl alcohol | 70.0 |
| Polyoxyethylene-oleyl alcohol | 2.0 |
| 1-Mnt | 0.1 |
| Perfume | Trace |
| Purified water | q.s. |

Production process: The above ingredients were evenly dissolved to provide a hair tonic for inhibiting gray hair.

Example 41

In this example, a hair tonic was prepared using α-hydroxy fatty acid fraction (S22). The formula is shown in Table 31.

TABLE 31

| Ingredient | | Amount |
|---|---|---|
| A | S22 | 5.0 |
| | Liquid paraffin | 20.0 |
| | Cetanol | 5.0 |
| | Sorbitan monostearate | 1.0 |
| | MSEOS | 1.0 |
| B | Preservative | Trace |
| | Purified water | q.s. |
| Purified water | | q.s. |

Production process: A and B were independently heated and evenly dissolved. Then, A was added to B and the resultant composition was cooled under constant agitation to provide a hair cream for inhibiting gray hair.

Example 42

In this example, a shampoo for inhibiting gray hair was prepared using α-hydroxy fatty acid fraction (S23). The formula is shown in Table 32.

TABLE 32

| Ingredient | Amount |
|---|---|
| S23 | 2.0 |
| LSHNa | 15.0 |
| LDEAM | 5.0 |
| DSAPEG | 2.0 |
| PAB | Trace |
| Perfume | Trace |

Production process: The above ingredients were evenly dissolved by heating and, then, cooled to provide a shampoo for inhibiting gray hair.

Example 43

In this example, a rinse for inhibiting gray hair was prepared using α-hydroxy fatty acid fraction (S20). The formula is shown in Table 33.

TABLE 33

| Ingredient | | Amount |
|---|---|---|
| A | S20 | 1.0 |
| | Stearyltrimethylammonium chloride | 1.0 |
| | Stearyl alcohol | 4.0 |
| | GLYMSA | 2.0 |
| | P70 | 2.0 |
| B | Purified water | q.s. |
| | PG | 5.0 |
| | PAB | Trace |

Production process: A and B were independently dissolved evenly by heating. The, A was added to B and the resultant composition was allowed to cool under constant agitation to provide a rise for inhibiting gray hair.

Production examples for sterol esters and formulation examples of cosmetic products (Examples 44–48) are shown below.

Production Example 1

A 2-liter 4-necked flask equipped with a stirrer, thermometer, nitrogen inlet pipe and water trap was charged with 300 g of the non-hydroxy fatty acid fraction (S19) of Example 11 and 370 g of cholesterol. Then, 1% of p-toluenesulfonic acid based on the non-hydroxy fatty acid charge was added as the catalyst and the reaction was carried out under nitrogen sparging and stirring at 120°–200° C. for about 5 hours. After completion of reaction, the catalyst was neutralized with sodium carbonate and the mixture was decolorized with active clay and filtered to remove the clay and catalyst. Then, the system was deodorized by blowing steam at 200° C. under reduced pressure and, at the same time, the unreacted cholesterol was removed to provide 592.4 g of the objective non-hydroxy fatty acid cholesterol ester (S24).

Production Example 2

The flask described in Production Example 1 was charged with 300 g of the α-hydroxy fatty acid fraction (S20) of Example 11 and 367.3 g of cholesterol and the procedure of Production Example 1 was then followed to provide 542.0 g of the objective α-hydroxy fatty acid cholesterol ester (S25).

The general properties of S24 and S25 obtained above are shown in Table 34.

TABLE 34

| Sample code | S24 | S25 |
|---|---|---|
| Acid value | 0.1 | 0.4 |
| Saponification value | 80.4 | 89.0 |
| Hydroxyl value | 17.8 | 76.2 |
| Melting point (°C.) | 55.6 | 45.2 |
| Color (GH) | $\leq 1$ | $\leq 1$ |

Example 44 Preparation of a W/O skin cream

| S25 | 1.0% |
|---|---|
| Lecithin | 0.5 |
| Petrolatum | 15.0 |
| YOFCO FE-1 (Note 1) | 10.0 |
| Water | Balance |

(Note 1):
A liquid oil prepared and purified by fractionating molecular-distilled lanolin fatty acid 2-octyldodecyldecanol ester; manufactured by Yoshikawa Oil and Fat Co., Ltd.).

Using the above ingredients, a W/O skin cream having satisfactory properties was prepared.

Example 45 Preparation of an O/W milk lotion

| S24 | 0.2% |
|---|---|
| P70 | 8.0 |
| Lecithin | 2.0 |
| Water | Balance |

Using the above ingredients, an O/W emulsion having satisfactory properties was prepared.

Example 46 Skin-care cream

| P70 | 50.0% |
|---|---|
| Beeswax | 15.0 |
| S24 | 5.0 |
| Borax | 0.8 |
| Water | Balance |
| Perfume | q.s. |

Using the above ingredients, a skin-care cream having satisfactory properties was prepared.

Example 47 Cold cream

| | |
|---|---|
| S25 | 1.5% |
| White petrolatum | 1.5 |
| YOFCO FE-101 (Note 2) | 1.5 |
| Beeswax | 2.0 |
| SA | 10.0 |
| TEA | 1.5 |
| GLY | 8.0 |
| Magnesium stearate | 20.0 |
| Water | Balance |

(Note 2):
A solid paste-like oil prepared by fractional purification of molecular-distilled lanolin fatty acid 2-octyldodecanol ester; Yoshikawa Oil and Fat Co., Ltd.).

Using the above ingredients, a cold cream with satisfactory properties was prepared.

Example 48 Rouge

| | |
|---|---|
| Oleyl alcohol | 25.6% |
| Cetanol | 5.0 |
| Castor oil | 31.0 |
| Beeswax | 6.0 |
| Petrolatum | 5.0 |
| CAWAX | 5.0 |
| S25 | 4.0 |
| Lanolin | 10.0 |
| Eosin acid | 0.4 |
| Color | 8.0 |
| Perfume | q.s. |

Using the above ingredients, a rouge with satisfactory properties was prepared.

As part of the evaluation of the invention, a panel of 10 female testers was instructed to use-test the product containing S24. The test procedure was as follows. The sample was applied to the dorsal part of the hand at bedtime and the spreadability at application and absorption into the skin of the product and whether an undesirable greasy handle remained on the skin surface or not were investigated. Moreover, the smoothness and non-greasy moist feel on the next morning were investigated. As a result, almost all the testers found that because of its good absorption into the skin on application, the product does not entail an uncomfortable liquid feel and recognized the good skin texture on waking, indicating that the objects of the invention has been fully accomplished.

Below given are production examples for the 2-ethylhexanol esters of the invention, production examples (Comparative Examples) for the corresponding esters starting with lanolin fatty acid and, thereafter, formulation examples (Examples 49–52) of the esters.

Production Example 3

A 1-liter four-necked flask equipped with a stirrer, thermometer, nitrogen gas inlet pipe and water trap was charged with 316 g of non-hydroxy fatty acid fraction (S19) and 143 g of 2-ethylhexanol, followed by addition of 5 g of p-toluenesulfonic acid as the catalyst. The reaction was conducted under nitrogen gas sparging at 100°–150° C. for 5 hours. After completion of reaction, the catalyst was neutralized with sodium carbonate and the reaction product was decolorized with active clay, filtered and deodorized by blowing steam under reduced pressure at 150° C. to provide 405 g of the objective non-hydroxy fatty acid 2-ethylhexanol ester (S26).

Production Example 4

The flask described in Production Example 3 was charged with 320 g of α-hydroxy fatty acid methyl ester (acid value 0.9, saponification value 175.4, OH value 167.9, m.p. 32.4° C.) and 143 g of 2-ethylhexanol followed by addition of 2 g of sodium methoxide as the catalyst. The reaction was conducted under nitrogen gas sparging at 100°–150° C. for 5 hours. After completion of reaction, the catalyst was removed by rinsing in the conventional manner, decolorized with active clay and filtered. The filtrate was steamed under reduced pressure at 150° C. to provide 400 g of the objective α-hydroxy fatty acid 2-ethylhexanol ester (S27).

Comparative Example 21

The reaction and purification procedures of Production Example 3 were repeated except that 300 g of distilled lanolin fatty acid (acid value 187, OH value 42.7, m.p. 49.2) was used in lieu of non-hydroxy fatty acid (S19). The yield of distilled lanolin fatty acid 2-ethylhexanol ester (S28) was 390 g.

The general analyses of the esters produced in Production Examples 3 and 4 and Comparative Example 21 are shown in Table 35.

TABLE 35

| | General analyses | | | | |
|---|---|---|---|---|---|
| | AV | SV | OHV | POV | CP |
| S26 | 0.1 | 139.5 | 4.2 | 1.2 | 19° C. |
| S27 | 0.6 | 137.8 | 114.9 | 1.8 | 9° C. |
| S28 | 0.1 | 141.8 | 30.2 | 2.1 | 13° C. |

The specific gravity and viscosity values of the esters produced in Production Examples 3 and 4 and Comparative Example 21 are shown in Table 36.

TABLE 36

| | General properties | |
|---|---|---|
| | Specific gravity (40° C.) | Viscosity (40° C.) |
| S26 | 0.8643 | 13.8 cst |
| S27 | 0.8910 | 22.1 cst |
| S28 | 0.8712 | 14.4 cst |

The non-hydroxy fatty acid esters are low in specific gravity and viscosity and insure a light feel without a sticky handle when incorporated in cosmetic products.

Table 37 shows the compatibilities of the esters produced in Production Examples 3 and 4 and Comparative Example 21 with the solvent, oil and liquid paraffin (5 g/100 ml).

TABLE 37

| | Compatibility of esters | | |
|---|---|---|---|
| 5 g/100 ml | S26 | S27 | S28 |
| 99.5%, Ethanol (20° C./2 days) | x (Precipitated) | o (Clear) | Δ (Slightly clouded) |
| 95.0%, Ethanol (20° C./2 days) | x (Precipitated) | o (Clear) | x (Precipitated) |
| Olive oil (10° C./2 days) | o (Clear) | o (Clear) | o (Clear) |
| Liquid paraffin (P-70) (−5° C./2 days) | o (Clear) | x (Precipitated) | x (Clouded) |

The compatibility test data presented in Table 37 indicate that the non-hydroxy fatty acid 2-ethylhexanol ester is highly compatible with non-polar liquid paraffin even at low temperature. On the other hand, the α-hydroxy fatty acid 2-ethylhexanol ester is highly soluble in polar solvents and well miscible with aqueous ethanol (95.0% ethanol). Generally in actual formulations employing a solubilizer, a greater compatibility can be expected.

Example 49 Preparation of a cream

| | |
|---|---|
| Squalane | 23.0% |
| Cetanol | 7.0 |
| Cholesterol | 2.0 |
| S27 | 10.0 |
| dl-α-Tocopherol acetate | 0.2 |
| Sorbitan monostearate | 3.5 |
| Polyoxyethylene (EO20)-sorbitan monostearate | 6.5 |
| Propylene glycol | 5.0 |
| p-Hydroxybenzoic ester | 0.2 |
| Perfume | Trace |
| Purified water | 42.6 |
| Total | 100.0 |

A cream was prepared according to the above formula. This cream was a W/O cream with a satisfactory luster and a long shelf life, providing for good intimacy to the skin.

Example 50 Preparation of a hair cream

| | |
|---|---|
| Oil phase | |
| Beeswax | 3.0% |
| Liquid paraffin | 15.0 |
| Microcrystalline wax | 5.0 |
| Behenyl alcohol | 1.0 |
| S26 | 15.0 |
| Polyoxyethylene(20) behenyl ether | 2.0 |
| Polyoxyethylene(40)-sorbitol tetraoleate | 1.0 |
| Monoglyceryl stearate | 2.5 |
| Antioxidant | q.s. |
| Water phase | |
| 1,3-Butylene glycol | 5.0% |
| Preservative/antimicrobial agent | q.s. |
| Perfume | q.s. |
| Purified water to make | 100.0% |

A hair cream was prepared according to the above formula. The resultant hair cream was a delicate milk lotion type W/O cream which remained stable for a long time and was not sticky in use, giving a soft feel.

Example 51 Preparation of a hair oil

| | |
|---|---|
| Liquid paraffin (70 seconds) | 33.0% |
| Castor oil | 33.0 |
| S26 | 34.0 |
| Perfume | q.s. |
| Perfume solubilizer | q.s. |
| Color and antioxidant | q.s. |

A hair oil was prepared according to the above formula. The resulting hair oil was not sticky in use and gave an appropriate sheen to the hair.

Example 52 Preparation of an ointment type oil foundation

| | |
|---|---|
| Base | |
| Liquid paraffin | 13.0% |
| S27 | 15.0 |
| Octyldodecanol | 7.0 |
| Lanolin acetate | 4.0 |
| Microcrystalline wax | 12.0 |
| Ceresine | 7.0 |
| Stearic monoethanolamide | 2.0 |
| Antioxidant, preservative and antimicrobial agent | q.s. |
| Color | |
| Titanium dioxide | 15.0 |
| Talc | 15.0 |
| Kaolin | 6.0 |
| Inorganic pigment | 4.0 |
| Perfume | q.s. |

An ointment type oil foundation was prepared according to the above formula. The resultant oil foundation was well spreadable on the skin and adherent, preserving the makeup well.

For comparison between the product of the invention and the conventional product, control preparations 22, 23, 24 and 25 corresponding to Examples 49, 50, 51 and 52, respectively, were prepared using S28 in lieu of S26 and S27 and these products were compared in regard to the feeling of use.

In this comparison test, 10 females were enrolled for testing the products of the invention as obtained in Examples 49 and 52 in terms of the feeling of use. For the products of the invention as obtained in Examples 50 and 51, 10 males were enrolled as testers of the feeling of use.

As to the products of the invention as obtained in Examples 49 and 52, all the female testers found that they were more intimate to the skin and had a non-greasy and moist feel. Regarding the products of the invention as obtained in Examples 50 and 51, all the males found that they were not sticky but provides a non-greasy feeling of use.

Some examples of production of the pentaerythritol and dipentaerythritol esters and some examples of preparation of cosmetic products containing them (Examples 53–55) are presented below.

Production Examples 5

Using the same equipment as used in Production Example 1, 150 g (0.56 mole) of non-hydroxy fatty acid (acid value 202.4, saponification value 203.7, OH value 14.9, m.p. 35.7° C.) and 38.1 g (0.28 mole) of pentaerythritol were reacted with stirring in a nitrogen stream at 220° C.–240° C. for 2–3 hours. After confirming that the acid value became not more than 2, the reaction mixture was allowed to cool to 80° C. and 4 g of active clay and 0.5 g of filter aid were added. The mixture was further stirred at the same temperature for about 30 minutes. Thereafter, the mixture was pressure-filtered to provide 178 g of non-hydroxy fatty acid pentaerythritol ester (S29).

Using lanolin fatty acid (LF) in lieu of the above fatty acid, the above procedure was otherwise repeated to give lanolin fatty acid pentaerythritol ester (LFP).

Production Example 6

In the same manner as Production Example 5, 150 g (0.56 mole) of the same non-hydroxy fatty acid was reacted with 47.4 g (0.19 mole) of dipentaerythritol in a nitrogen stream at 220° C.–240° C. for 2–3 hours. After confirming that the acid value became not more than 2, the reaction mixture was allowed to cool to 80° C. and 4 g of active clay and 0.5 g of filter aid were added. The mixture was further stirred at the same temperature for about 30 minutes, after which it was pressure-filtered to recover 187.5 g of non-hydroxy fatty acid dipentaerythritol ester (S30).

Production Example 7

By the same procedure as described in Production Example 5, 150 g (0.49 mole) of α-hydroxy fatty acid (S22) was reacted with 34.0 g (0.25 mole) of pentaerythritol to prepare 168 g of α-hydroxy fatty acid pentaerythritol ester (S31).

Production Example 8

By the same procedure as described in Production Example 5, 150 g (0.49 mole) of S22 was reacted with 40.6 g (0.16 mole) of dipentaerythritol to prepare 175 g of α-hydroxy fatty acid dipentaerythritol ester (S32).

The analyses of the esters obtained in the above Production Examples 5, 6 and 7 are shown in Table 38.

TABLE 38

| Sample code | General analyses | | | | |
|---|---|---|---|---|---|
| | GH | AV | SV | OHV | MP (°C.) |
| S29 | 2 | 1.6 | 178.0 | 165.1 | 30.5 |
| S30 | 2 | 1.2 | 157.8 | 226.9 | 44.2 |
| S31 | 4 | 2.0 | 170.0 | 192.0 | 45.2 |
| S32 | 4 | 2.0 | 145.6 | 235.6 | 58.2 |
| LEP | 8 | 4.6 | 154.8 | 140.6 | 45.0 |

Example 53

Using the esters obtained in Production Examples 5, 6, 7 and 8 for the evaluation of their usefulness as emulsifying agents, W/O creams were prepared according to the following formula and their stability and feeling of use were evaluated. The results are presented in Table 39.

The feeling of use represents the result of organoleptic evaluation by 10 testers (mean values are shown). This evaluation was made according to the following rating schedule using the pentaerythritol ester of the lanolin fatty acid which had not been fractionated into non-hydroxy fatty acid and α-hydroxy fatty acid (LFP) as the reference.

⊙: Markedly improved o: Almost equivalent to LFP x: Not improved

Cream formula

| Oil phase A | |
|---|---|
| Emulsifier | 20.0% |
| Cetanol | 15.0 |
| Ozocerite | 30.0 |
| Solid paraffin | 20.0 |
| Petrolatum | 20.0 |
| Liquid paraffin | 250.0 |
| Water phase B | |
| Magnesium sulfate | 5.0 |
| Glycerol | 30.0 |
| Water | 608.0 |
| Perfume | 2.0 |

Production process: The above oil phase A ingredients and water phase B ingredients were respectively blended and heated to 70° C. and B was gradually added to A under stirring. The stirring was further continued for a while, after which the mixture was homogenized well with a homomixer and allowed to cool to room temperature under agitation.

TABLE 39

Stability and feeling of use of creams

| Type of cream | Emulsion stability | Feeling of use | | |
|---|---|---|---|---|
| | | Spread-ability | Moist feel | Non-greasy feel |
| S29 composition | Excellent | ⊙ | o | ⊙ |
| S30 composition | Excellent | ⊙ | o | ⊙ |
| S31 composition | Excellent | ⊙ | ⊙ | o |
| S32 composition | Excellent | ⊙ | ⊙ | o |
| LA composition | Good | o | o | o |
| LFP composition | Good | o | o | o |
| LF composition | Not emulsifiable | x | x | x |

Example 54

Tables 40, 41 and 42 show the emollient lotions, creams and rouges containing S29 through S32 and, as controls, the corresponding products containing LFP or LA instead.

TABLE 40

| | Emollient lotions | | | | | |
|---|---|---|---|---|---|---|
| Ingredient | Formula 1 | Formula 2 | Formula 3 | Formula 4 | Control 1 | Control 2 |
| A S29 | 2.0 | — | — | — | — | — |
| S30 | — | 2.0 | — | — | — | — |
| S31 | — | — | 2.0 | — | — | — |
| S32 | — | — | — | 2.0 | — | — |
| LFP | — | — | — | — | 2.0 | — |
| LA | — | — | — | — | — | 2.0 |
| Stearic acid | 0.2 | 0.2 | 0.2 | 0.2 | 0.2 | 0.2 |
| Cetanol | 1.5 | 1.5 | 1.5 | 1.5 | 1.5 | 1.5 |
| Petrolatum | 3.0 | 3.0 | 3.0 | 3.0 | 3.0 | 3.0 |
| P70 | 10.0 | 10.0 | 10.0 | 10.0 | 10.0 | 10.0 |
| MOEO | 2.0 | 2.0 | 2.0 | 2.0 | 2.0 | 2.0 |
| Perfume | 0.4 | 0.4 | 0.4 | 0.4 | 0.4 | 0.4 |

TABLE 40-continued

| | | Emollient lotions | | | | | |
|---|---|---|---|---|---|---|---|
| | Ingredient | Formula 1 | Formula 2 | Formula 3 | Formula 4 | Control 1 | Control 2 |
| | Preservative | q.s. | q.s. | q.s. | a.s. | q.s. | q.s. |
| B | Glycerol | 3.0 | 3.0 | 3.0 | 3.0 | 3.0 | 3.0 |
| | PG | 5.0 | 5.0 | 5.0 | 5.0 | 5.0 | 5.0 |
| | TEA | 1.0 | 1.0 | 1.0 | 1.0 | 1.0 | 1.0 |
| | Purified water | 70.0 | 70.0 | 70.0 | 70.0 | 70.0 | 70.0 |
| | Total | 100.0 | 100.0 | 100.0 | 100.0 | 100.0 | 100.0 |

Production process: The above A and B ingredients were respectively blended and warmed to 70° C. and B was added to A under agitation. The mixture was further stirred for a while, after which it was evenly homogenized using a homomixer and allowed to cool to room temperature under constant agitation.

TABLE 41

| | | Creams | | | | | |
|---|---|---|---|---|---|---|---|
| | Ingredient | Formula 5 | Formula 6 | Formula 7 | Formula 8 | Control 3 | Control 4 |
| A | S29 | 3.5 | — | 1 | — | — | — |
| | S30 | — | 3.5 | — | — | — | — |
| | S31 | — | — | 3.5 | — | — | — |
| | S32 | — | — | — | 3.5 | — | — |
| | LFP | — | — | — | — | 3.5 | — |
| | LA | — | — | — | — | — | 3.5 |
| | Squalane | 23.0 | 23.0 | 23.0 | 23.0 | 23.0 | 23.0 |
| | Cetanol | 7.0 | 7.0 | 7.0 | 7.0 | 7.0 | 7.0 |
| | CHO | 2.0 | 2.0 | 2.0 | 2.0 | 2.0 | 2.0 |
| | ODL | 10.0 | 10.0 | 10.0 | 10.0 | 10.0 | 10.0 |
| | TCP | 0.2 | 0.2 | 0.2 | 0.2 | 0.2 | 0.2 |
| | MSEOS | 6.5 | 6.5 | 6.5 | 6.5 | 6.5 | 6.5 |
| B | PG | 5.0 | 5.0 | 5.0 | 5.0 | 5.0 | 5.0 |
| | POBZ | 0.2 | 0.2 | 0.2 | 0.2 | 0.2 | 0.2 |
| | Perfume | q.s. | q.s. | q.s. | q.s. | q.s. | q.s. |
| | Purified water | 42.6 | 42.6 | 42.6 | 42.6 | 42.6 | 42.6 |
| | Total | 100.0 | 100.0 | 100.0 | 100.0 | 100.0 | 100.0 |

Production process: The same process as used for Formula 1.

TABLE 42

| | Rouges | | | | | |
|---|---|---|---|---|---|---|
| Ingredient | Formula 9 | Formula 10 | Formula 11 | Formula 12 | Control 5 | Control 6 |
| Base | | | | | | |
| S29 | 6.0 | — | — | — | — | — |
| S30 | — | 6.0 | — | — | — | — |
| S31 | — | — | 6.0 | — | — | — |
| S32 | — | — | — | 6.0 | — | — |
| LFP | — | — | — | — | 6.0 | — |
| LA | — | — | — | — | — | 6.0 |
| OALC | 25.6 | 25.6 | 25.6 | 25.6 | 25.6 | 25.6 |
| Cetanol | 5.0 | 5.0 | 5.0 | 5.0 | 5.0 | 5.0 |
| Castor oil | 31.0 | 31.0 | 31.0 | 31.0 | 31.0 | 31.0 |
| Beeswax | 8.0 | 8.0 | 8.0 | 8.0 | 8.0 | 8.0 |
| Petrolatum | 5.0 | 5.0 | 5.0 | 5.0 | 5.0 | 5.0 |

TABLE 42-continued

| | Rouges | | | | | |
|---|---|---|---|---|---|---|
| Ingredient | Formula 9 | Formula 10 | Formula 11 | Formula 12 | Control 5 | Control 6 |
| Carnauba wax | 7.0 | 7.0 | 7.0 | 7.0 | 7.0 | 7.0 |
| CLEH | 4.0 | 4.0 | 4.0 | 4.0 | 4.0 | 4.0 |
| Eosin acid | 0.4 | 0.4 | 0.4 | 0.4 | 0.4 | 0.4 |
| Color | 8.0 | 8.0 | 8.0 | 8.0 | 8.0 | 8.0 |
| Perfume | q.s. | q.s. | q.s. | q.s. | q.s. | q.s. |
| Total | 100.0 | 100.0 | 100.0 | 100.0 | 100.0 | 100.0 |

Production process: The base ingredients were admixed and melted evenly. Then, the color was added and dispersed well by kneading with a roll moll, then remelted, defoamed, cast in a container and quenched to solidity.

A panel of 10 testers was requested to use-test the emollient lotions, creams and rouges prepared to the above formulas. The results of this sensory evaluation (mean results are shown) are presented in Table 7.

TABLE 43

| Texture and feeling of sue of the formulations | | | | |
|---|---|---|---|---|
| Formula No. | Texture of product | Spreadability on skin or lips | Non-greasy feel | Moist feel |
| Formula 1 | ⊙ | ⊙ | ⊙ | ○ |
| Formula 2 | ⊙ | ⊙ | ⊙ | ○ |
| Formula 3 | ⊙ | ⊙ | ○ | ⊙ |
| Formula 4 | ⊙ | ⊙ | ○ | ⊙ |
| Control 1 | ○ | ○ | ○ | ○ |
| Control 2 | x | x | x | x |
| Formula 5 | ⊙ | ⊙ | ⊙ | ○ |
| Formula 6 | ⊙ | ⊙ | ⊙ | ○ |
| Formula 7 | ⊙ | ⊙ | ○ | ⊙ |
| Formula 8 | ⊙ | ⊙ | ○ | ⊙ |
| Control 3 | ○ | ○ | ○ | ○ |
| Control 4 | x | x | x | x |
| Formula 9 | ⊙ | ⊙ | ⊙ | ○ |
| Formula 10 | ⊙ | ⊙ | ⊙ | ○ |
| Formula 11 | ⊙ | ⊙ | ○ | ⊙ |
| Formula 12 | ⊙ | ⊙ | ○ | ⊙ |
| Control 5 | ○ | ○ | ○ | ○ |
| Control 6 | x | x | x | x |

Example 55

Hair solids and hair creams were prepared using S29 through S32 and their feeling of use was compared with that of control products prepared using LFP or LA.

The results are shown in Tables 44 and 45, respectively.

TABLE 44

| | Hair solids | | | | | |
|---|---|---|---|---|---|---|
| Ingredient | Formula 13 | Formula 14 | Formula 15 | Formula 16 | Control 7 | Control 8 |
| S29 | 2.7 | — | — | — | — | — |
| S30 | — | 2.7 | — | — | — | — |
| S31 | — | — | 2.7 | — | — | — |
| S32 | — | — | — | 2.7 | — | — |
| LFP | — | — | — | — | 2.7 | — |
| LA | — | — | — | — | — | 2.7 |
| P70 | 20.0 | 20.0 | 20.0 | 20.0 | 20.0 | 20.0 |
| LEEO3 | 5.0 | 5.0 | 5.0 | 5.0 | 5.0 | 5.0 |
| LEEO23 | 6.0 | 6.0 | 6.0 | 6.0 | 6.0 | 5.0 |
| LDEAM | 6.0 | 6.0 | 6.0 | 6.0 | 6.0 | 6.0 |
| Purified water | 60.3 | 60.3 | 60.3 | 60.3 | 60.3 | 60.3 |
| Total | 100.0 | 100.0 | 100.0 | 100.0 | 100.0 | 100.0 |

TABLE 45

| Ingredient | Hair creams | | | | | |
|---|---|---|---|---|---|---|
| | Formula 17 | Formula 18 | Formula 19 | Formula 20 | Control 9 | Control 10 |
| Oil phase | | | | | | |
| S29 | 15.0 | — | — | — | — | — |
| S30 | — | 15.0 | — | — | — | — |
| S31 | — | — | 15.0 | — | — | — |
| S32 | — | — | — | 15.0 | — | — |
| LFP | — | — | — | — | 15.0 | — |
| LA | — | — | — | — | — | 15.0 |
| Beeswax | 3.0 | 3.0 | 3.0 | 3.0 | 3.0 | 3.0 |
| P70 | 15.0 | 15.0 | 15.0 | 15.0 | 15.0 | 15.0 |
| MCWAX | 5.0 | 5.0 | 5.0 | 5.0 | 5.0 | 5.0 |
| BEA-LC | 1.0 | 1.0 | 1.0 | 1.0 | 1.0 | 1.0 |
| EOBA20 | 2.0 | 2.0 | 2.0 | 2.0 | 2.0 | 2.0 |
| TOEOS | 1.0 | 1.0 | 1.0 | 1.0 | 1.0 | 1.0 |
| GLYMSA | 2.5 | 2.5 | 2.5 | 2.5 | 2.5 | 2.5 |
| BHT | q.s. | q.s. | q.s. | q.s. | q.s. | q.s. |
| Water phase | | | | | | |
| BG | 5.0 | 5.0 | 5.0 | 5.0 | 5.0 | 5.0 |
| PAB | q.s. | q.s. | q.s. | q.s. | q.s. | q.s. |
| Perfume | q.s. | q.s. | q.s. | q.s. | q.s. | q.s. |
| Purified water | 50.5 | 50.5 | 50.5 | 50.0 | 50.0 | 50.0 |
| Total | 100.0 | 100.0 | 100.0 | 100.0 | 100.0 | 100.0 |

Ten female (aged 19–55 years) and 10 male (aged 20–65 years) panelists were requested to use-test the above hair solids and hair lotions. The results for the formulations of the invention and the control formulations are shown in Table 46.

TABLE 46

| Formula No. | Sheen of hair | | Manageability | | Feeling of use | |
|---|---|---|---|---|---|---|
| | Good | Not good | Good | Not good | Good | Not good |
| Formula 13 | 18 | 2 | 18 | 2 | 18 | 2 |
| Formula 14 | 16 | 4 | 16 | 4 | 16 | 4 |
| Formula 15 | 15 | 5 | 12 | 8 | 15 | 5 |
| Formula 16 | 15 | 5 | 12 | 8 | 15 | 5 |
| Control 7 | 8 | 12 | 8 | 12 | 10 | 10 |
| Control 8 | 4 | 16 | 5 | 15 | 4 | 16 |
| Formula 17 | 16 | 4 | 16 | 4 | 16 | 4 |
| Formula 18 | 15 | 5 | 15 | 5 | 15 | 5 |
| Formula 19 | 12 | 8 | 13 | 7 | 12 | 8 |
| Formula 20 | 13 | 7 | 14 | 6 | 13 | 7 |
| Control 9 | 9 | 11 | 8 | 12 | 10 | 10 |
| Control 10 | 6 | 14 | 6 | 14 | 6 | 14 |

Some examples of production of glycerol esters and some formulation examples (Examples 56–58) of cosmetics containing the esters are presented below.

It should be understood that the esterification reaction between the non-hydroxy fatty acid and glycerol or the hydroxy fatty acid and glycerol provides mono-, di- and tri-esters and a mixed ester. By the ordinary process, there is obtained a product comprising 30–90% of monoester, 30–50% of diester and 1–15% of triester.

Production Example 9

Using the same equipment as described in Production Example 1, 120 g of the same non-hydroxy fatty acid as that used in Production Example 5 was melted by heating in a nitrogen stream and 1.11 g of tetraethylammonium iodide was added. When the temperature reached 106° C., 49.7 g of glycidol was added over a period of 3 hours. After completion of addition, the reaction mixture was allowed to ripen at 106°–110° C. After completion of reaction, the reaction mixture was allowed to cool to 80° C. and 5 g of active clay and 1.2 g of filter aid were added. The whole mixture was stirred for about 30 minutes, after which it was pressure-filtered to provide 160 g of non-hydroxy fatty acid glyceride (S33).

A lanolin fatty acid glyceride (LFGL) was prepared by the same procedure except that lanolin fatty acid was used in lieu of the above fatty acid.

Production Example 10

Using the flask described in Production Example 1, 120 g of non-hydroxy fatty acid (S19) was reacted with 18.4 g of glycerol at 200° C. for 5 hours. The reaction mixture was then pressure-filtered as in Production Example 9 to provide 101.6 g of non-hydroxy fatty acid glyceride (S34).

Production Example 11

To 120 g of a non-hydroxy fatty acid methyl ester (saponification value 194.4, OH value 19.3, cloud point 19.0° C.), as the fatty acid, was added 14.0 g of glycerol. Then, 1.6 g of sodium methoxide was added as the catalyst and the reaction was conducted at 150°–200° C. for 4 hours. The reaction mixture was then pressure-filtered as in Production Example 1 to provide 72 g of non-hydroxy fatty acid glyceride (S35).

Production Example 12

The reaction described in Production Example 1 was carried out except that 45.3 g of glycidol was used as the fatty acid in lieu of 120 g of S22 and the reaction mixture was then pressure-filtered to provide 158 g of α-hydroxy fatty acid glyceride (S36).

Production Example 13

As in Production Example 9, 19.1 g of glycerol was added to 120 g of hydroxy fatty acid (acid value 184.0, OH value 165.0, m.p. 63.3° C.) and the reaction was conducted in a nitrogen stream at 160°–200° C. for 3 hours. The reaction mixture was then pressure-filtered to provide 92.8 g of hydroxy fatty acid glyceride (S37).

Production Example 14

The flask described in Production Example 1 was charged with 120 g of hydroxy fatty acid methyl ester (saponification value 179.5, OH value 111.4, m.p. 28.0° C.) and 38.9 g of glycerol and the reaction was conducted as in Production Example 3 to provide 93.0 g of hydroxy fatty acid glyceride (S38).

The analyses of the esters obtained in Production Examples 9 through 14 are shown in Table 47.

TABLE 47

| | General analyses | | | |
|---|---|---|---|---|
| Sample | GH | AV | SV | OHV |
| S33 | 2 | 0.7 | 151.9 | 289.5 |
| S34 | 2 | 4.9 | 160.5 | 169.5 |
| S35 | 3+ | 0.6 | 191.7 | 49.9 |
| S36 | 2 | 0.6 | 148.4 | 291.5 |
| S37 | 3+ | 5.7 | 161.5 | 285.1 |
| S38 | 3+ | 1.4 | 176.6 | 179.2 |
| LFGL | 6 | 0.6 | 147.6 | 103.8 |

Example 56

For testing the water solubility of each of the samples prepared in Production Examples 9 through 14, the condition of the sample on addition of water was investigated. The results are shown in Table 48. For this test, 2 g of each sample was dissolved by heating in a beaker, 100 ml of distilled water at 70° C. was added and the mixture was stirred at the constant temperature of 70° C. for about 1 hour, after which it was allowed to cool and examined.

TABLE 48

| | Interaction with water | |
|---|---|---|
| Sample | Condition of aqueous solution | Stability |
| S33 | Liquid crystal | Stable for at least 3 months |
| S34 | Emulsion | Phase separation |
| S35 | Emulsion | Phase separation |
| S36 | Liquid crystal | Stable for at least 3 months |
| S37 | Emulsion | Stable for at least 3 months |
| S38 | Emulsion | Phase separation |
| GLYMSA | Emulsion | Phase separation on standing at room temperature |

The stearic monoglyceride (GLYMSA) used was Excel manufactured by Kao Corporation.

Example 57

Examples of the hand cream, cleansing cream and rouge formulations including S33 through S38 or, as controls, LFGL and LA are presented in Tables 49, 50 and 51, respectively.

TABLE 49

| | Hand creams | | | |
|---|---|---|---|---|
| Ingredient | Formula 1 | Formula 2 | Formula 3 | Formula 4 |
| A S33 | 12.0 | — | — | — |
| S34 | — | 12.0 | — | — |
| S35 | — | — | 12.0 | — |
| S36 | — | — | — | 12.0 |
| S37 | — | — | — | — |
| S38 | — | — | — | — |
| LA | — | — | — | — |
| LFGL | — | — | — | — |
| Cetanol | 2.0 | 2.0 | 2.0 | 2.0 |
| P70 | 1.0 | 1.0 | 1.0 | 1.0 |
| B GLY | 10.0 | 10.0 | 10.0 | 10.0 |
| PAB | 0.1 | 0.1 | 0.1 | 0.1 |
| Perfume | 0.4 | 0.4 | 0.4 | 0.4 |
| Purified water | 74.5 | 74.5 | 74.5 | 74.5 |
| Total | 100.0 | 100.0 | 100.0 | 100.0 |
| Ingredient | Formula 5 | Formula 6 | Control 1 | Control 2 |
| A S33 | — | — | — | — |
| S34 | — | — | — | — |
| S35 | — | — | — | — |
| S36 | — | — | — | — |
| S37 | 12.0 | — | — | — |
| S38 | — | 12.0 | — | — |
| LA | — | 12.0 | — | — |
| LFGL | — | — | — | 12.0 |
| Cetanol | 2.0 | 2.0 | 2.0 | 2.0 |
| P70 | 1.0 | 1.0 | 1.0 | 1.0 |
| B GLY | 10.0 | 10.0 | 10.0 | 10.0 |
| PAB | 0.1 | 0.1 | 0.1 | 0.1 |
| Perfume | 0.4 | 0.4 | 0.4 | 0.4 |
| Purified water | 74.5 | 74.5 | 74.5 | 74.5 |
| Total | 100.0 | 100.0 | 100.0 | 100.0 |

Production process: The above A and B ingredients were respectively blended and warmed to 70° C. and B was gradually added to A under constant stirring. The stirring was continued for a while, after which the mixture was emulsified well with a homomixer. The emulsion was then allowed to cool under agitation.

TABLE 50

| | Cleansing creams | | | |
|---|---|---|---|---|
| Ingredient | Formula 7 | Formula 8 | Formula 9 | Formula 10 |
| A S33 | 10.0 | — | — | — |
| S34 | — | 10.0 | — | — |
| S35 | — | — | 10.0 | — |
| S36 | — | — | — | 10.0 |
| S37 | — | — | — | — |
| S38 | — | — | — | — |
| LA | — | — | — | — |
| LFGL | — | — | — | — |
| P70 | 30.0 | 30.0 | 30.0 | 30.0 |
| Beeswax | 10.0 | 10.0 | 10.0 | 10.0 |
| B Borax | 0.5 | 0.5 | 0.5 | 0.5 |
| PAB | Trace | Trace | Trace | Trace |
| Perfume | Trace | Trace | Trace | Trace |
| Purified water | 49.5 | 49.5 | 49.5 | 49.5 |
| Total | 100.0 | 100.0 | 100.0 | 100.0 |

TABLE 50-continued

Cleansing creams

| Ingredient | | Formula 11 | Formula 12 | Control 3 | Control 4 |
|---|---|---|---|---|---|
| A | S33 | — | — | — | — |
| | S34 | — | — | — | — |
| | S35 | — | — | — | — |
| | S36 | — | — | — | — |
| | S37 | 10.0 | — | — | — |
| | S38 | — | 10.0 | — | — |
| | LA | — | — | 10.0 | — |
| | LFGL | — | — | — | 10.0 |
| | P70 | 30.0 | 30.0 | 30.0 | 30.0 |
| | Beeswax | 10.0 | 10.0 | 10.0 | 10.0 |
| B | Borax | 0.5 | 0.5 | 0.5 | 0.5 |
| | PAB | Trace | Trace | Trace | Trace |
| | Perfume | Trace | Trace | Trace | Trace |
| | Purified water | 49.5 | 49.5 | 49.5 | 49.5 |
| | Total | 100.0 | 100.0 | 100.0 | 100.0 |

Production process: The same as used for Formula 1.

TABLE 51

Rouges

| Ingredient | Formula 13 | Formula 14 | Formula 15 | Formula 16 |
|---|---|---|---|---|
| Base | | | | |
| S33 | 6.0 | — | — | — |
| S34 | — | 6.0 | — | — |
| S35 | — | — | 6.0 | — |
| S36 | — | — | — | 6.0 |
| S37 | — | — | — | — |
| S38 | — | — | — | — |
| LA | — | — | — | — |
| LFGL | — | — | — | — |
| OALC | 25.6 | 25.6 | 25.6 | 25.6 |
| Cetanol | 5.0 | 5.0 | 5.0 | 5.0 |
| Castor oil | 31.0 | 31.0 | 31.0 | 31.0 |
| Beeswax | 8.0 | 8.0 | 8.0 | 8.0 |
| Petrolatum | 5.0 | 5.0 | 5.0 | 5.0 |
| Carnauba wax | 7.0 | 7.0 | 7.0 | 7.0 |
| CLEH | 4.0 | 4.0 | 4.0 | 4.0 |
| Eosin acid | 0.4 | 0.4 | 0.4 | 0.4 |
| Color | 8.0 | 8.0 | 8.0 | 8.0 |
| Perfume | q.s. | q.s. | q.s. | q.s. |
| Total | 100.0 | 100.0 | 100.0 | 100.0 |

| Ingredient | Formula 17 | Formula 18 | Control 5 | Control 6 |
|---|---|---|---|---|
| Base | | | | |
| S33 | — | — | — | — |
| S34 | — | — | — | — |
| S35 | — | — | — | — |
| S36 | — | — | — | — |
| S37 | 6.0 | — | — | — |
| S38 | — | 6.0 | — | — |
| LA | — | — | 6.0 | — |
| LFGL | — | — | — | 6.0 |
| Cetanol | 5.0 | 5.0 | 5.0 | 5.0 |
| Castor oil | 31.0 | 31.0 | 31.0 | 31.0 |
| Beeswax | 8.0 | 8.0 | 8.0 | 8.0 |
| Petrolatum | 5.0 | 5.0 | 5.0 | 5.0 |
| Carnauba wax | 7.0 | 7.0 | 7.0 | 7.0 |
| CLEH | 4.0 | 4.0 | 4.0 | 4.0 |
| Eosin acid | 0.4 | 0.4 | 0.4 | 0.4 |
| Color | 8.0 | 8.0 | 8.0 | 8.0 |

TABLE 51-continued

Rouges

| | | | | |
|---|---|---|---|---|
| Perfume | q.s. | q.s. | q.s. | q.s. |
| Total | 100.0 | 100.0 | 100.0 | 100.0 |

Production process: The base ingredients were blended and evenly melted by heating. The color was then added and evenly dispersed by kneading with a roll mill and the composition was remelted, defoamed, cast in a container and quenched to solidify.

Ten panelists were requested to use-test the hand creams, cleansing creams and rouges of the above formulas. The results of this sensory test are shown in Table 52 (mean ratings by panelists are shown).

TABLE 52

Texture and feeling of use of formulations

| Formula No. | Texture | Spreadability on skin or lips | Freedom from greasiness | Moist feel |
|---|---|---|---|---|
| Formula 1 | ⊙ | ⊙ | ⊙ | ○ |
| Formula 2 | ⊙ | ⊙ | ⊙ | ○ |
| Formula 3 | ⊙ | ⊙ | ⊙ | ○ |
| Formula 4 | ⊙ | ⊙ | ○ | ⊙ |
| Formula 5 | ⊙ | ⊙ | ○ | ⊙ |
| Formula 6 | ⊙ | ⊙ | ○ | ⊙ |
| Control 1 | x | x | x | x |
| Control 2 | ○ | ○ | ○ | ○ |
| Formula 7 | ⊙ | ⊙ | ⊙ | ○ |
| Formula 8 | ⊙ | ⊙ | ⊙ | ○ |
| Formula 9 | ⊙ | ⊙ | ⊙ | ○ |
| Formula 10 | ⊙ | ⊙ | ○ | ⊙ |
| Formula 11 | ⊙ | ⊙ | ○ | ⊙ |
| Formula 12 | ⊙ | ⊙ | ○ | ⊙ |
| Control 3 | x | x | x | x |
| Control 4 | ○ | ○ | ○ | ○ |
| Formula 13 | ⊙ | ⊙ | ⊙ | ⊙ |
| Formula 14 | ⊙ | ⊙ | ⊙ | ○ |
| Formula 15 | ⊙ | ⊙ | ⊙ | ○ |
| Formula 16 | ⊙ | ⊙ | ○ | ⊙ |
| Formula 17 | ⊙ | ⊙ | ○ | ⊙ |
| Formula 18 | ⊙ | ⊙ | ○ | ⊙ |
| Control 5 | x | x | x | x |
| Control 6 | ○ | ○ | ○ | ○ |

Example 58

The basal liquid hair conditioner formula shown below in Table 53 was supplemented with one of S33 through S38, LFGL and LA and the resultant formulations were evaluated for feeling of use.

The results are shown in Table 53.

TABLE 53

Liquid hair conditioners

| Ingredient | Formula 19 | Formula 10 | Formula 21 | Formula 22 |
|---|---|---|---|---|
| S33 | 30 | — | — | — |
| S34 | — | 30 | — | — |
| S35 | — | — | 30 | — |
| S36 | — | — | — | 30 |
| S37 | — | — | — | — |
| S38 | — | — | — | — |
| LA | — | — | — | — |
| LFGL | — | — | — | — |
| Ethanol | 50 | 50 | 50 | 50 |
| Purified water | 20 | 20 | 20 | 20 |
| Perfume | Trace | Trace | Trace | Trace |

TABLE 53-continued

| | Liquid hair conditioners | | | |
|---|---|---|---|---|
| Color | Trace | Trace | Trace | Trace |
| Total | 100.0 | 100.0 | 100.0 | 100.0 |
| Ingredient | Formula 23 | Formula 24 | Control 7 | Control 8 |
| S33 | — | — | — | — |
| S34 | — | — | — | — |
| S35 | — | — | — | — |
| S36 | — | — | — | — |
| S37 | 30 | — | — | — |
| S38 | — | 30 | — | — |
| LA | — | — | 30 | — |
| LFGL | — | — | — | 30 |
| Ethanol | 50 | 50 | 50 | 50 |
| Purified water | 20 | 20 | 20 | 20 |
| Perfume | Trace | Trace | Trace | Trace |
| Color | Trace | Trace | Trace | Trace |
| Total | 100.0 | 100.0 | 100.0 | 100.0 |

Production process: The ingredients shown in Table 53 were vigorously stirred to mix and filtered to provide a product.

Ten female (aged 19–55 years) and 10 male (aged 20–65 years) panelists were instructed to use-test the liquid hair conditions obtained above. The results of the formulations of the invention and the control preparations are shown in Table 54.

TABLE 54

| | Sheen of hair | | Manageability | | Feeling of use | |
|---|---|---|---|---|---|---|
| Formula No. | Good | Not good | Good | Not good | Good | Not good |
| Formula 19 | 18 | 2 | 17 | 3 | 19 | 1 |
| Formula 20 | 18 | 2 | 17 | 3 | 19 | 1. |
| Formula 21 | 17 | 3 | 16 | 4 | 18 | 2 |
| Formula 22 | 18 | 2 | 17 | 3 | 18 | 2 |
| Formula 23 | 18 | 2 | 18 | 2 | 17 | 3 |
| Formula 24 | 18 | 2 | 17 | 3 | 17 | 3 |
| Control 7 | 4 | 16 | 3 | 17 | 2 | 18 |
| Control 8 | 0 | 20 | 0 | 20 | 1 | 19 |

Some examples of production of the sucrose esters of the invention and some examples of cosmetic formulations including the esters are presented below.

Production Example 15

To 342 g of sucrose was added 96 g of non-hydroxy fatty acid methyl ester (GH=1–, AV=0.3, SV=194.4, OHV=19.3, CP=19° C., IV=4.9, hydroxy fatty acid content=4.98%) and the mixture was dissolved in 1.5 l of DMF. After the solution was warmed to 60° C., 0.07 mole of sodium methoxide was added as the catalyst and the reaction was carried out at 60° C. for 3 hours. Then, ⅔ of the DMF was distilled off on a boiling water bath at 10–20 mmHg and the residue was extracted with 8 portions of 350 ml each of hexane to remove the unreacted methyl ester. The extraction residue was diluted with 5 volumes of acetone to precipitate and remove the unreacted sucrose and the acetone was distilled off. The residue was dissolved in 4 volumes of water and, after addition of 5% aqueous sodium chloride, the solution was heated to 90° C. The crude sucrose ester (100 g) separating out in the upper layer was separated and dried. This was further purified by silica gel column chromatography to provide 62 g of the sucrose ester (S39) as the IPA fraction.

The above procedure was repeated using α-hydroxy fatty acid methyl ester in lieu of the above fatty acid material to provide α-hydroxy fatty acid sucrose ester (S40).

The composition of each of the esters prepared above was analyzed by TLC-FID (Iatroscan, Yatron).

The ester compositions as well as the general analyses and properties of S39 and S40 are shown in Table 55.

TABLE 55

| | S39 | S40 |
|---|---|---|
| AV | 0.1 | 0.1 |
| SV | 118.7 | 108.2 |
| OHV | 523.0 | 663.0 |
| Transparent m.p. | 95.0 | 103.0 |
| Ester composition | | |
| Mono-ester | 64.1 | 76.0 |
| Di-ester | 7.3 | 8.5 |
| Tri-ester | 28.6 | 15.4 |

The compatibilities of S39 and S40 with various solvents are shown in Table 56. In the table, SC stands for clear solution, ST for translucent solution, P for partial solution (turbidity or partial precipitation), S for solidified and I for insoluble.

TABLE 56

| | | Compatibility | | | |
|---|---|---|---|---|---|
| | | S39 | | S40 | |
| Test substance | concentration (%) | 1% | 3% | 1% | 3% |
| Water | 20° C. | ST | ST | SC | ST |
| | 70° C. | ST | ST | SC | SC |
| EtOH95 | 20° C. | P | P | SC | P |
| | 70° C. | P | P | SC | P |
| PG | 20° C. | SC | SC | SC | SC |
| | 70° C. | SC | SC | SC | SC |
| OALC | 20° C. | SC | ST | ST | ST |
| | 70° C. | SC | SC | ST | SC |
| P70 | 20° C. | I | I | I | I |
| | 70° C. | I | I | I | I |

The above sucrose ester can be varied in monoester content by adjusting the reaction conditions to provide a series of products with varying HLB numbers. The sucrose esters are being used prevalently as safe hydrophilic emulsifiers in the food industry but can be used as surfactants for cosmetic products because they are dermatologically harmless, nontoxic to the living body and can be made available in a spectrum of surface activity suited for intended uses.

Example 59 Preparation of O/W emulsions

O/W emulsions were prepared according to the following formulas.

TABLE 57

| Ingredient | Formula 1 | Formula 2 |
|---|---|---|
| P70 | 20.0 | 20.0 |
| CEALC | 1.0 | 1.0 |
| S39 | 0.5 | — |
| S40 | — | 0.5 |

TABLE 57-continued

| Ingredient | Formula 1 | Formula 2 |
|---|---|---|
| SS6.5 | 3.0 | 3.0 |
| HYECE | 0.5 | 0.5 |
| PG | 4.0 | 4.0 |
| Purified water | 71.0 | 71.0 |

Production process: HYECE was dissolved in purified water and PG and the solution was heated to 80° C. On the other hand, P70, CEALC and sucrose ester were blended and heated to 80° C. under agitation. The above aqueous phase was gradually added to the oily phase and the mixture was further stirred for 15 minutes, after which it was allowed to cool under agitation to provide a cream.

The above procedure provides a stable emulsion which does not show the formation of particles which is often observed in O/W emulsions of this kind.

Example 60 Preparation of conditioning shampoos

The ingredients listed below were blended under mild heating and the mixture was adjusted to pH 6.0–6.5 to thereby provide a conditioning shampoo.

TABLE 58

| Ingredient | Formula 3 | Formula 4 |
|---|---|---|
| LHSAM | 10.0 | 15.0 |
| LADBE | 10.0 | 10.0 |
| PPG5 | 2.0 | 2.0 |
| S39 | 20.0 | — |
| S40 | — | 15.0 |
| PROTE | 2.0 | 2.0 |
| Purified water | 54.0 | 54.0 |

Incorporation of the sucrose ester results in the formation of shampoos having no irritation potential and a good hair moisturizing effect.

Production Example 16

By the same procedure as described in Production Example 1, 100 g of non-hydroxy fatty acid (free NH according to the invention; acid value=206.4, saponification value=208.6, GH=2, OHV=23.3, m.p.=33.6), 114 g of NJCOL 200A and 1 g of p-toluenesulfonic acid were reacted at 95°–100° C. for 4 hours. After the reaction, the catalyst and unreacted NH were neutralized and removed and the residue was rinsed to provide 200 g of non-hydroxy fatty acid NJCOL ester (S41).

The above procedure was repeated using the α-hydroxy fatty acid of the invention in lieu of the above fatty acid to provide 179 g of α-hydroxy fatty acid NJCOL ester (S42).

Moreover, the same procedure was repeated using 98.6 g of oleyl alcohol as the alcohol to provide 188 g of non-hydroxy fatty acid oleyl alcohol ester (S43).

The general analyses of the above esters are shown in Table 59.

TABLE 59

| | General analyses | | |
|---|---|---|---|
| | S41 | S42 | S43 |
| GH | ≦1 | ≦1 | ≦1 |
| AV | 0.1 | 0.1 | 0.1 |
| SV | 99.4 | 94.8 | 107.0 |
| OHV | 15.5 | 101.3 | 9.5 |
| POV | 1.0 | 0.9 | 1.0 |
| CP (cosmetic grade) | ≦−10° C. | 7° C. | 28° C. |
| Specific gravity (20° C.) | 0.858 | 0.874 | 0.863 |
| Viscosity (40° C.) | 23.1 cst | 36.3 cst | 20.5 cst |

The compatibilities (1 g/20 ml) of each ester with various solvents at specific temperatures are shown in Table 60 (the abbreviations of degrees of solubility are the same as used in Table 56).

TABLE 60

| | Compatibility | | | | | | | | |
|---|---|---|---|---|---|---|---|---|---|
| Ester | S41 | | | S42 | | | S43 | | |
| Solvent | ET | OO | P70 | ET | OO | P70 | ET | OO | P70 |
| 30° C. | SC | SC | SC | SC | SC | SC | SC | SC | SC |
| 20° C. | P | SC | SC | SC | SC | SC | P | SC | SC |
| 10° C. | | SC | SC | SC | SC | SC | | SC | SC |
| 5° C. | | SC | SC | SC | SC | SC | | P | SC |
| −5° C. | | S | SC | p | SC | SC | | S | P |
| −10° C. | | | SC | | S | SC | | | |

The cloud point (CP) of S41 was exceedingly low, viz. ≦−10° C., and this ester spreads well without resistance on application to the skin. S42 also has a low CP value and is characterized in that it is more compatible with polar solvents and oils than S41. Therefore, these esters not only find application as regular base oils but can be used as esters of low temperature fluidity capable of replacing liquid paraffin, which has a flow point of about −12° C., for exploitation of their excellent compatibility and high water vapor permeability as compared with liquid paraffin to provide very desirable cosmetic products insuring efficient skin respiration.

Where any cosmetic formulation includes polar ingredients such as olive and other vegetable oils, oleyl alcohol, etc., S42 may prove to be a better choice from compatibility points of view.

Example 61 Preparation of vanishing creams

Vanishing creams were prepared using S41 and S42 in lieu of S19 in the formula of Example 14 given in Table 6.

Example 62 Preparation of skin creams

Skin creams were prepared by using S41 and S42, both obtained above, in lieu of YOFCO FE-1 in Example 44.

Example 63 Preparation of foundations and rouges

Oleaginous ointment type foundations, milk lotion type foundations and rouges were prepared using S41 and 42, obtained above, in lieu of S7 in the formula of Example 20 in Table 10, the formula of Example 23 in Table 11 and the formula of Example 24 in Table 12.

The resultant cosmetic products were found, by panel tests, to be excellent in cream texture, spreadability on the skin and feeling of use.

Example 64 Preparation of hair creams

Hair creams were prepared using S41 and S42 in lieu of S5 in the formula of Example 30 shown in Table 16.

The resultant creams were found, by a panel test, to be excellent in hair sheen, hair manageability and feeling of use.

We claim:

1. A process for producing purified hydroxy fatty acids or $C_{1-4}$ lower alcohol esters thereof and purified non-hydroxy fatty acids or $C_{1-4}$ lower alcohol esters thereof from lanolin fatty acids comprising the steps of:

i) reacting in a non-aquous medium lanolin fatty acids, $C_{1-4}$ lower alcohol esters thereof, or mixtures thereof with solid boric acid to convert the hydroxy fatty acids or $C_{1-4}$ lower alcohol esters thereof to boric acid esters thus forming a mixture containing the boric acid esters and unreacted non-hydroxy fatty acids or $C_{1-4}$ lower alcohol esters thereof, and ii) separating the non-hydroxy fatty acids or $C_{1-4}$ lower alcohol esters thereof from the boric acid esters of hydroxy fatty acids or $C_{1-4}$ lower alcohol esters thereof by vacuum distillation.

2. The purified non-hydroxy fatty acids or $C_{1-4}$ lower alcohol esters thereof obtained by the process of claim 1.

3. The process according to claim 1, further comprising the steps of hydrolyzing the boric acid esters of hydroxy fatty acids or $C_{1-4}$ lower alcohol esters thereof to hydroxy fatty acids or $C_{1-4}$ lower alcohol esters thereof and separating the hydroxy fatty acids or $C_{1-4}$ lower alcohol esters thereof.

4. The purified hydroxy fatty acids or $C_{1-4}$ lower alcohol esters thereof obtained by the process of claim 3.

5. The process according to claim 3, further comprising the step of separating α-hydroxy fatty acids or $C_{1-4}$ lower alcohol esters thereof from ω-hydroxy fatty acids or $C_{1-4}$ lower alcohol esters thereof by vacuum distillation.

6. The purified α-hydroxy fatty acids or $C_{1-4}$ lower alcohol esters thereof obtained by the process of claim 5.

7. The purified ω-hydroxy fatty acids or $C_{1-4}$ lower alcohol esters thereof obtained by the process of claim 5.

8. A cosmetic or pharmaceutical composition for external use comprising the α-hydroxy fatty acids or $C_{1-4}$ lower alcohol esters thereof of claim 6.

9. A cosmetic or pharmaceutical composition for external use comprising the ω-hydroxy fatty acids or $C_{1-4}$ lower alcohol esters thereof of claim 7.

10. The composition of claim 4 wherein said hydroxy fatty acid has been converted to an ester derivative selected from the group consisting of $C_{1-4}$ lower alcohol esters, sterol esters, sugar esters, 2-ethyl-hexanol esters, higher alcohol esters and polyhydric alcohol esters.

11. The composition of claim 7 wherein said ω-hydroxy fatty acid has been converted to an ester derivative selected from the group consisting of $C_{1-4}$ lower alcohol esters, sterol esters, sugar esters, 2-ethyl-hexanol esters, higher alcohol esters and polyhydric alcohol esters.

12. A composition comprising non-hydroxy fatty acids or $C_{1-4}$ lower alcohol esters thereof obtained from lanolin fatty acids, having a hydroxy fatty acid content of less than 10% by weight, comprising 30–45% by weight of $C_{10-30}$ iso-fatty acids or $C_{1-4}$ lower alcohol esters thereof, 30–50% by weight of $C_{11-31}$ anteiso-fatty acids or $C_{1-4}$ lower alcohol esters thereof and 10–30% by weight of $C_{10-30}$ normal-fatty acids or $C_{1-4}$ lower alcohol esters thereof, the amount of the iso-fatty acids or $C_{1-4}$ lower alcohol esters thereof and anteiso-fatty acids or $C_{1-4}$ lower alcohol esters thereof being at least 60% by weight of the composition.

13. A cosmetic or pharmaceutical composition for external use comprising the non-hydroxy fatty acids or $C_{1-4}$ lower alcohol esters thereof of claim 12.

14. The composition of claim 12 wherein said non-hydroxy fatty acid has been converted to an ester derivative selected from the group consisting of $C_{1-4}$ lower alcohol esters, sterol esters, sugar esters, 2-ethyl-hexanol esters, higher alcohol esters and polyhydric alcohol esters.

15. The composition of claim 12 wherein said non-hydroxy fatty acid has been converted to an ester derivative thereof.

16. A composition comprising hydroxy fatty acids or $C_{1-4}$ lower alcohol esters thereof obtained from lanolin fatty acids, having an ω-hydroxy fatty acid content of 0–15%, and at least 60% by weight of α-hydroxy fatty acids or $C_{1-4}$ lower alcohol esters thereof having not less than 14 carbon atoms; said α-hydroxy fatty acids or $C_{1-4}$ lower alcohol esters thereof comprising 50–70% by weight of normal α-hydroxy fatty acids or $C_{1-4}$ lower alcohol esters thereof, 10–30% by weight of iso-α-hydroxy fatty acids or $C_{1-4}$ lower alcohol esters thereof, and 0–15% by weight of anteiso-α-hydroxy fatty acids or $C_{1-4}$ lower alcohol esters thereof.

17. A cosmetic or pharmaceutical composition for external use comprising the hydroxy fatty acids or $C_{1-4}$ lower alcohol esters thereof of claim 16.

18. The composition of claim 16 wherein said hydroxy fatty acid has been converted to an ester derivative selected from the group consisting of $C_{1-4}$ lower alcohol esters, sterol esters, sugar esters, 2-ethyl-hexanol esters, higher alcohol esters and polyhydric alcohol esters.

19. The composition of claim 16 wherein said hydroxy fatty acid has been converted to an ester derivative thereof.

* * * * *

UNITED STATES PATENT AND TRADEMARK OFFICE
CERTIFICATE OF CORRECTION

PATENT NO.: 5,556,970
DATED : September 17, 1996
INVENTOR(S): KAWASAKI et al.

It is certified that an error appears in the above-identified patent and that said Letters Patent is hereby corrected as shown below:

On the title page on the patent in item [73], change the Assignee "Yoshikawa Oil & Fat Co., Ltd.," to --Nippon Fine Chemical Co., Ltd.,--.

Signed and Sealed this

Tenth Day of April, 2001

*Attest:*

NICHOLAS P. GODICI

*Attesting Officer*  *Acting Director of the United States Patent and Trademark Office*